US011312690B2

(12) United States Patent
Clark et al.

(10) Patent No.: US 11,312,690 B2
(45) Date of Patent: Apr. 26, 2022

(54) COMPOUNDS, COMPOSITIONS, METHODS FOR TREATING DISEASES, AND METHODS FOR PREPARING COMPOUNDS

(71) Applicant: UNIVERSITY OF LOUISVILLE RESEARCH FOUNDATION, INC., Louisville, KY (US)

(72) Inventors: Geoffrey J. Clark, Pewee Valley, KY (US); John O. Trent, Louisville, KY (US); Joseph A. Burlison, Louisville, KY (US); Nagaraju Miriyala, Louisville, KY (US)

(73) Assignee: University of Lousville Research Foundation, Inc., Louisville, KY (US)

( * ) Notice: Subject to any disclaimer, the term of this patent is extended or adjusted under 35 U.S.C. 154(b) by 725 days.

(21) Appl. No.: 15/746,819

(22) PCT Filed: Jul. 22, 2016

(86) PCT No.: PCT/US2016/043660
§ 371 (c)(1),
(2) Date: Jan. 23, 2018

(87) PCT Pub. No.: WO2017/019537
PCT Pub. Date: Feb. 2, 2017

(65) Prior Publication Data
US 2020/0079742 A1 Mar. 12, 2020

Related U.S. Application Data

(60) Provisional application No. 62/196,336, filed on Jul. 24, 2015.

(51) Int. Cl.
*C07D 239/95* (2006.01)
*A61P 35/04* (2006.01)

(52) U.S. Cl.
CPC ............ *C07D 239/95* (2013.01); *A61P 35/04* (2018.01)

(58) Field of Classification Search
CPC .............................. C07D 239/95; A61P 35/04
USPC ...................................................... 514/266.4
See application file for complete search history.

(56) References Cited

U.S. PATENT DOCUMENTS

| | | | | |
|---|---|---|---|---|
| 3,475,429 A * | 10/1969 | Eberhard | ............. | C07D 495/04 544/117 |
| 4,146,716 A * | 3/1979 | Cox | ..................... | C07D 333/38 544/278 |
| 9,062,026 B2 * | 6/2015 | Zhou | ..................... | C07D 473/34 |
| 2007/0027156 A1 * | 2/2007 | Nakai | ..................... | A61P 43/00 514/246 |
| 2008/0207614 A1 | 8/2008 | Lee et al. | | |

FOREIGN PATENT DOCUMENTS

| | | | | |
|---|---|---|---|---|
| CN | 1761671 A | 4/2006 | | |
| CN | 101263124 A | 9/2008 | | |
| DE | 10104097 A1 * | 8/2002 | .......... | A61K 31/519 |
| EP | 1167367 A1 | 1/2002 | | |
| JP | 2001139556 A | 5/2001 | | |
| JP | 2002105082 A | 4/2002 | | |
| WO | 2002/000664 A1 | 1/2002 | | |
| WO | 2004/065391 A1 | 8/2004 | | |
| WO | WO-2005026126 A1 * | 3/2005 | .......... | C07D 487/04 |
| WO | 2007/011618 A1 | 1/2007 | | |
| WO | 2007/011623 A1 | 1/2007 | | |
| WO | 2011/121418 A1 | 10/2011 | | |
| WO | 2013/165320 A1 | 11/2013 | | |
| WO | 2014/081718 A1 | 5/2014 | | |

OTHER PUBLICATIONS

JP 2001139556 (A) (May 22, 2001)—English language abstract from Espacenet, 1 page.
JP 2002105082 (A) (Apr. 10, 2002)—English language abstract from Espacenet, 1 page.
Nepomuceno et al. (2015) "Synthesis and Evaluation of Quinazolines as Inhibitors of the Bacterial Cell Division Protein FtsZ" ACS Med. Chem. Lett., vol. 6, pp. 308-312.
Vaidya et al. (1981) "Studies in Benzofurans: Part XII-Synthesis & Reactions of 2-Chloromethyl-3,4-dihydro-4-oxobenzofuro[3,2-d]pyrimidine" Indian Journal of Chemistry, vol. 20B, pp. 780-783.
_PCT/US2016/043660, International Search Report dated Oct. 19, 2016, 3 pages.
_PCT/US2016/043660, Written Opinion dated Oct. 19, 2016, 4 pages.
Ahn et al., "Mitochondria as biosynthetic factories for cancer proliferation" Cancer Metab (2015) vol. 3, Article 1, 10 pages.
Baines et al., "Inhibition of Ras for cancer treatment: the search continues" Future Med Chem (2011) vol. 3, pp. 1787-1808.
Bodemann et al., "Rai GTPases and cancer: linchpin support of the tumorigenic platform" Nat Rev Cancer (2008) vol. 8, pp. 133-140.
Bogolubsky et al., "Synthesis of Thieno[2,3-d]pyrimidin-2-ylmethanamine Combinatorial Library with Four Diversity Points" J. Comb. Chem. (2007) vol. 9, pp. 661-667.

(Continued)

*Primary Examiner* — Kahsay Habte
(74) *Attorney, Agent, or Firm* — ALGM LLP; Harry J. Guttman

(57) ABSTRACT

Some embodiments of the invention include inventive compounds (e.g., compounds of Formula (I)). Other embodiments include compositions (e.g., pharmaceutical compositions) comprising the inventive compound. Still other embodiments of the invention include compositions (e.g., pharmaceutical compositions) for treating, for example, certain diseases using the inventive compounds. Some embodiments include methods of using the inventive compound (e.g., in compositions or in pharmaceutical compositions) for administering and treating (e.g., diseases such as cancer). Further embodiments include methods for making the inventive compounds. Additional embodiments of the invention are also discussed herein.

40 Claims, 12 Drawing Sheets

(56) References Cited

OTHER PUBLICATIONS

Bos, "All in the family? New insights and questions regarding interconnectivity of Ras, Rap1 and Ral" The EMBO Journal (1998) vol. 17, No. 23, pp. 6776-6782.
Buday et al., "Many faces of Ras activation" Biochim Biophys Acta (2008) vol. 1786, pp. 178-187.
Chien et al., "RalB GTPase-mediated activation of the IkappaB family kinase TBK1 couples innate immune signaling to tumor cell survival" Cell (2006) vol. 127, pp. 157-170.
Colburn et al., "Correlation of anchorage-independent growth with tumorigenicity of chemically transformed mouse epidermal cells" Cancer Res (1978) vol. 38, pp. 624-634.
Dailey et al., "Structure-based drug design: from nucleic acid to membrane protein targets" Exp Mol Pathol (2009) vol. 86, No. 3, pp. 141-150.
Donninger et al., "NORE1A is a Ras senescence effector that controls the apoptotic/senescent balance of p53 via HIPK2" Journal of Cell Biology (2015) vol. 208, No. 6, pp. 777-789.
Donninger et al., "The Ras effector RASSF2 controls the PAR-4 tumor suppressor" Mol Cell Biol (2010) vol. 30, pp. 2608-2620.
Elam et al., "RRP22 is a farnesylated, nucleolar, Ras-related protein with tumor suppressor potential" Cancer Res (2005) vol. 65, pp. 3117-3125.
Ellis et al., "Tamoxifen and the farnesyl transferase inhibitor FTI-277 synergize to inhibit growth in estrogen receptor-positive breast tumor cell lines" Breast Cancer Res Treat (2003) vol. 78, pp. 59-67.
Eser et al., "Oncogenic KRAS signalling in pancreatic cancer" Br J Cancer (2014) vol. 111, pp. 817-822.
Ferro et al., "RalGDS family members couple Ras to Ral signalling and that's not all" Cell Signal (2010) vol. 22, No. 12, pp. 1804-1810.
Gonzalez-Garcia et al., "RalGDS is required for tumor formation in a model of skin carcinogenesis" Cancer Cell (2005) vol. 7, pp. 219-226.
Hahn et al., "Creation of human tumour cells with defined genetic elements" Nature (1999) vol. 400, pp. 464-468.
Hamad et al., "Distinct requirements for Ras oncogenesis in human versus mouse cells" Genes Dev (2002) vol. 16, pp. 2045-2057.
Hidalgo et al., "A pilot clinical study of treatment guided by personalized tumorgrafts in patients with advanced cancer" Mol Cancer Ther (2011) vol. 10, pp. 1311-1316.
Hudson et al., "Targeted noninvasive imaging of EGFR-expressing orthotopic pancreatic cancer using multispectral optoacoustic tomography" Cancer Res (2014) vol. 74, No. 21, pp. 6271-6279.
Kashatus et al., "RALA and RALBP1 regulate mitochondrial fission at mitosis" Nat Cell Biol (2011) vol. 13, pp. 1108-1115.
Kimbrough et al., "Orthotopic pancreatic tumors detected by optoacoustic tomography using Syndecan-1" J Surg Res (2015) vol. 193, No. 1, pp. 246-254.
Klebe, "Applying thermodynamic profiling in lead finding and optimization" Nat Rev Drug Discov (2015) vol. 14, pp. 95-110.
Lamb et al., "Antibiotics that target mitochondria effectively eradicate cancer stem cells, across multiple tumor types: Treating cancer like an infectious disease" Oncotarget (2015) vol. 6, No. 7, pp. 4569-4584.
Lim et al., "Activation of RalA is critical for Ras-induced tumorigenesis of human cells" Cancer Cell (2005) vol. 7, pp. 533-545.
Lim et al., "Divergent roles for RalA and RalB in malignant growth of human pancreatic carcinoma cells" Curr Biol (2006) vol. 16, No. 24, pp. 2385-2394.
Liu et al., "The role of the exocyst in matrix metalloproteinase secretion and actin dynamics during tumor cell invadopodia formation" Mol Biol Cell (2009) vol. 20, No. 16, pp. 3763-3771.
Matulis et al., "Thermodynamic stability of carbonic anhydrase: measurements of binding affinity and stoichiometry using ThermoFluor." Biochemistry (2005) vol. 44, pp. 5258-5266.
Mitin et al., "Signaling interplay in Ras superfamily function" Curr Biol. (2005) vol. 15, No. 14, pp. R563-R574.
Morris et al., "KRAS, Hedgehog, Wnt and the twisted developmental biology of pancreatic ductal adenocarcinoma" Nat Rev Cancer (2010) vol. 10, pp. 683-695.
Neel et al., "The RalGEF-Ral Effector Signaling Network: The Road Less Traveled for Anti-Ras Drug Discovery" Genes Cancer (2011) vol. 2, No. 3, pp. 275-287.
Nicolson, "Tumor microenvironment: paracrine and autocrine growth mechanisms and metastasis to specific sites" Front Radiat Ther Oncol (1994) vol. 28, pp. 11-24.
Nicolson et al., "Brain metastasis: role of trophic, autocrine, and paracrine factors in tumor invasion and colonization of the central nervous system" Curr Top Microbiol Immunol (1996) vol. 213, No. 2, pp. 89-115.
O'Hayer et al., "A genetically defined normal human somatic cell system to study ras oncogenesis in vivo and in vitro" Methods Enzymol (2006) vol. 407, pp. 637-647.
Perez-Mancera et al., "What we have learned about pancreatic cancer from mouse models" Gastroenterology (2012) vol. 142, pp. 1079-1092.
Pylayeva-Gupta et al., "RAS oncogenes: weaving a tumorigenic web" Nat Rev Cancer (2011) vol. 11, pp. 761-774.
Rangarajan et al., "Species-and cell type-specific requirements for cellular transformation" Cancer Cell (2004) vol. 3, pp. 171-183.
Seguin et al., "An integrin beta(3)-KRAS-RalB complex drives tumour stemness and resistance to EGFR inhibition" Nat Cell Biol (2014) vol. 16, No. 5, pp. 457-468.
Smith et al., "Transcriptional Signatures of Ral GTPase Are Associated with Aggressive Clinicopathologic Characteristics in Human Cancer" Cancer Res (2012) vol. 72, No. 14, pp. 3480-3491.
Toruner et al., "Antianoikis effect of nuclear factor-kappaB through up-regulated expression of osteoprotegerin, BCL-2, and IAP-1" J Biol Chem (2006) vol. 281, No. 13, pp. 8686-8696.
Vigil et al., "Aberrant overexpression of the Rgl2 Ral small GTPase-specific guanine nucleotide exchange factor promotes pancreatic cancer growth through Ral-dependent and Ral-independent mechanisms" J Biol Chem (2010a) vol. 285, pp. 34729-34740.
Vigil et al., "Ras superfamily GEFs and GAPs: validated and tractable targets for cancer therapy?" Nat Rev Cancer (2010b) vol. 10, No. 12, pp. 842-857.
Ward et al., "Signal pathways which promote invasion and metastasis: critical and distinct contributions of extracellular signal-regulated kinase and Ral-specific guanine exchange factor pathways" Mol Cell Biol (2001) vol. 21, No. 17, pp. 5958-5969.
Xia, "Surface markers of cancer stem cells in solid tumors" Curr Stem Cell Res Ther (2014) vol. 9, No. 2, pp. 102-111.
Xie et al., "Exocyst sec5 regulates exocytosis of newcomer insulin granules underlying biphasic insulin secretion" PLoS ONE (2013) vol. 8, Issue 7, No. e67561, 8 pages.

* cited by examiner

IB RalGDS

IB β-actin shvec    shRalGDS

IP GFP
IB HA

IB HA (K-Ras12V)

IP GFP (RalGDS)
IB GFP

COMPOUNDS, COMPOSITIONS, METHODS FOR TREATING DISEASES, AND METHODS FOR PREPARING COMPOUNDS

CROSS-REFERENCE TO RELATED APPLICATIONS

This application is a National Stage Entry of International Application No. PCT/US2016/043660 filed Jul. 22, 2016, entitled "COMPOUNDS, COMPOSITIONS, METHODS FOR TREATING DISEASES, AND METHODS FOR PREPARING COMPOUNDS" which is herein incorporated by reference in its entirety, and which claims the benefit of U.S. Provisional Application No. 62/196,336, filed Jul. 24, 2015, entitled "RAS INHIBITORS, RALGDS INHIBITORS, RELATED COMPOSITIONS, AND THEIR USES TO TREAT DISEASE" which is herein incorporated by reference in its entirety.

GOVERNMENT RIGHTS

This invention was made with government support under 1U01HL127518-01 awarded by National Institutes of Health. The government has certain rights in the invention.

BACKGROUND

Some Ras protein mutations can give rise to cancer. Over 90% of pancreatic tumors appear to be associated with some Ras protein mutations. In certain instances, when Ras protein is bound by GTP, Ras guanine nucleotide exchange factors (RasGEFs) appear to activate Ras-like (Ral) proteins by promoting Ral protein binding to GTP. Activated Ral proteins can sometimes enhance the development of cancer, including tumorigenesis and metastasis. There are four members of the RalGEF family: Ral guanine nucleotide dissociation stimulator (RalGDS), RGL1, RGL2, and RGL3.

Several compounds are known to treat cancer, but do so inadequately. For example, many attempts to develop a clinically effective Ras inhibitor have failed. There appear to be no reported inhibitors of RalGEFs.

Certain embodiments of the invention address one or more of the deficiencies described above. For example, in some embodiments of the invention, inventive compounds such as Formula (I) are disclosed. In some embodiments, RalGEF inhibitors are disclosed. Other embodiments include compositions (e.g., pharmaceutical compositions) comprising the inventive compound. Still other embodiments of the invention include compositions (e.g., pharmaceutical compositions) for treating, for example, certain diseases using the inventive compounds. Some embodiments include methods of using the inventive compound (e.g., in compositions or in pharmaceutical compositions) for administering and treating (e.g., diseases such as cancer). Further embodiments include methods for making the inventive compounds. Additional embodiments of the invention are also discussed herein.

SUMMARY

Some embodiments of the present invention include a compound selected from Formula (I):

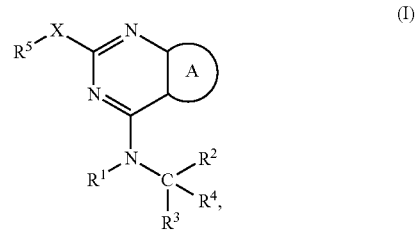

salts, optical isomers, geometric isomers, salts of isomers, and derivatives thereof. In some embodiments, $R^1$ is H, $C_1$-$C_3$ alkyl, $C_2$-$C_3$ alkenyl, or $C_2$-$C_3$ alkynyl, which $C_1$-$C_3$ alkyl, $C_2$-$C_3$ alkenyl, or $C_2$-$C_3$ alkynyl is optionally substituted with one or more of halogen, hydroxy (—OH), methanoyl (—COH), carboxy (—$CO_2$H), ethynyl (—CCH), cyano (—CN), sulfo (—$SO_3$H), methyl, or ethyl; $R^2$ is H, halogen, hydroxy (—OH), cyano (—CN), sulfo (—$SO_3$H), $C_1$-$C_3$ alkyl, $C_2$-$C_3$ alkenyl, $C_2$-$C_3$ alkynyl, or $C_1$-$C_2$ alkoxy, which $C_1$-$C_3$ alkyl, $C_2$-$C_3$ alkenyl, $C_2$-$C_3$ alkynyl, or $C_1$-$C_2$ alkoxy is optionally substituted with one or more of halogen, hydroxy (—OH), methanoyl (—COH), carboxy (—$CO_2$H), ethynyl (—CCH), cyano (—CN), sulfo (—$SO_3$H), methyl, or ethyl; $R^3$ is H, halogen, hydroxy (—OH), cyano (—CN), sulfo (—$SO_3$H), $C_1$-$C_3$ alkyl, $C_2$-$C_3$ alkenyl, $C_2$-$C_3$ alkynyl, or $C_1$-$C_2$ alkoxy, which $C_1$-$C_3$ alkyl, $C_2$-$C_3$ alkenyl, $C_2$-$C_3$ alkynyl, or $C_1$-$C_2$ alkoxy is optionally substituted with one or more of halogen, hydroxy (—OH), methanoyl (—COH), carboxy (—$CO_2$H), ethynyl (—CCH), cyano (—CN), sulfo (—$SO_3$H), methyl, or ethyl; $R^4$ is H, halogen, —CN, hydroxy (—OH), methanoyl (—COH), carboxy (—$CO_2$H), $C_1$-$C_7$ alkyl, $C_2$-$C_7$ alkenyl, $C_2$-$C_7$ alkynyl, $C_1$-$C_6$ alkoxy, cycloalkyl, heterocyclyl, aryl, or heteroaryl, which methanoyl (—COH), carboxy (—$CO_2$H), $C_1$-$C_7$ alkyl, $C_2$-$C_7$ alkenyl, $C_2$-$C_7$ alkynyl, $C_1$-$C_6$ alkoxy, cycloalkyl, heterocyclyl, aryl, or heteroaryl is optionally substituted with one or more of halogen, oxo (=O), hydroxy (—OH), methanoyl (—COH), carboxy (—$CO_2$H), nitro (—$NO_2$), —$NH_2$, —$N(CH_3)_2$, cyano (—CN), ethynyl (—CCH), propynyl, sulfo (—$SO_3$H), morpholinyl, —CO-morpholin-4-yl, phenyl, —$CONH_2$, —$CON(CH_3)_2$, $C_1$-$C_3$ alkyl, $C_1$-$C_3$ perfluoronated alkyl, or $C_1$-$C_3$ alkoxy; $R^5$ is H, halogen, —CN, hydroxy (—OH), methanoyl (—COH), carboxy (—$CO_2$H), $C_1$-$C_7$ alkyl, $C_2$-$C_7$ alkenyl, $C_2$-$C_7$ alkynyl, $C_1$-$C_6$ alkoxy, cycloalkyl, heterocyclyl, aryl, or heteroaryl, which methanoyl (—COH), carboxy (—$CO_2$H), $C_1$-$C_7$ alkyl, $C_2$-$C_7$ alkenyl, $C_2$-$C_7$ alkynyl, $C_1$-$C_6$ alkoxy, cycloalkyl, heterocyclyl, aryl, or heteroaryl is optionally substituted with one or more of halogen, oxo (=O), hydroxy (—OH), methanoyl (—COH), carboxy (—$CO_2$H), nitro (—$NO_2$), —$NH_2$, —$N(CH_3)_2$, cyano (—CN), ethynyl (—CCH), propynyl, sulfo (—$SO_3$H), morpholinyl, —CO-morpholin-4-yl, —$CONH_2$, —$CON(CH_3)_2$, $C_1$-$C_3$ alkyl, $C_1$-$C_3$ perfluoronated alkyl, or $C_1$-$C_3$ alkoxy; X is a bivalent $C_1$-$C_7$ alkyl where 1, 2, or 3 of the $C_1$-$C_7$ alkyl carbons is optionally replaced with a hetero atom which can be the same or different if more than one carbon atom is replaced, and which $C_1$-$C_7$ alkyl or any of the hetero atom replacements, as chemically appropriate, is optionally substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, —CONH$_2$, —CON(CH$_3$)$_2$, C$_1$-C$_3$ alkyl, C$_1$-C$_3$ perfluorinated alkyl, or C$_1$-C$_3$ alkoxy; and ring A is a monocyclic or bicyclic ring comprising 1, 2, 3, 4, or 5 double bonds and 4, 5, 6, 7, 8, 9, or 10 carbon atoms, where 1, 2, 3, 4, or 5 of the non-fusion carbon atoms, can be optionally replaced with a hetero atom (e.g., N, O, S) which can be the same or different if more than one carbon atom is replaced, which ring A carbon atoms or any of the hetero atom replacements, as chemically appropriate, can optionally be substituted with one or more of halogen, oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, —CONH$_2$, —CON(CH$_3$)$_2$, C$_1$-C$_6$ alkyl, C$_1$-C$_6$ perfluorinated alkyl (e.g., trifluoromethyl or perfluoroethyl), or C$_1$-C$_5$ alkoxy, and wherein the fusion carbon atoms are single bonded or double bonded to each other. In certain embodiments, R$^1$ is H or C$_1$-C$_3$ alkyl, which C$_1$-C$_3$ alkyl is optionally substituted with one or more of halogen, hydroxy (—OH), methanoyl (—COH), carboxy (—CO$_2$H), cyano (—CN), ethynyl (—CCH), sulfo (—SO$_3$H), methyl, or ethyl. In other embodiments, R$^1$ is H, methyl, ethyl, perfluorinated methyl, or perfluorinated ethyl. In some embodiments, R$^2$ is H, halogen, hydroxy (—OH), C$_1$-C$_3$ alkyl, or C$_1$-C$_2$ alkoxy, which C$_1$-C$_3$ alkyl or C$_1$-C$_2$ alkoxy is optionally substituted with one or more of halogen, hydroxy (—OH), methanoyl (—COH), carboxy (—CO$_2$H), cyano (—CN), ethynyl (—CCH), sulfo (—SO$_3$H), methyl, or ethyl. In other embodiments, R$^2$ is H, halogen, hydroxy (—OH), cyano (—CN), sulfo (—SO$_3$H), methyl, ethyl, methoxy, perfluorinated methyl, or perfluorinated ethyl. In some embodiments, R$^3$ is H, halogen, hydroxy (—OH), C$_1$-C$_3$ alkyl, or C$_1$-C$_2$ alkoxy, which C$_1$-C$_3$ alkyl or C$_1$-C$_2$ alkoxy is optionally substituted with one or more of halogen, hydroxy (—OH), methanoyl (—COH), carboxy (—CO$_2$H), cyano (—CN), ethynyl (—CCH), sulfo (—SO$_3$H), methyl, or ethyl. In other embodiments, R$^3$ is H, halogen, hydroxy (—OH), cyano (—CN), sulfo (—SO$_3$H), methyl, ethyl, methoxy, perfluorinated methyl, or perfluorinated ethyl. In some embodiments, R$^4$ is H, halogen, —CN, hydroxy (—OH), methanoyl (—COH), carboxy (—CO$_2$H), C$_1$-C$_7$ alkyl, C$_1$-C$_6$ alkoxy, cycloalkyl, heterocyclyl, aryl, or heteroaryl, which methanoyl (—COH), carboxy (—CO$_2$H), C$_1$-C$_7$ alkyl, C$_1$-C$_6$ alkoxy, cycloalkyl, heterocyclyl, aryl, or heteroaryl is optionally substituted with one or more of halogen, oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluorinated alkyl, or C$_1$-C$_3$ alkoxy. In yet other embodiments, R$^4$ is Cl, hydroxy (—OH), methyl, ethyl, C$_{1-5}$ alkyl, C$_3$ alkyl, —CN, ethynyl, —CONH$_2$, —CON(CH$_3$)$_2$, 2-(morpholinyl)ethoxy, —CO-morpholin-4-yl, ethoxy, methoxy, 5-hydroxy pyridyl, 5-hydroxy pyrid-3-yl, indolyl, 1-indolyl, 1,2,3,4-tetrahydroisoquinolyl, 2-1,2,3,4-tetrahydroisoquinolyl, 1,2-methylenedioxyphenyl, 2,3-methylenedioxyphenyl, furyl, 2-furyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, benzyl, pyridyl, 3-pyridyl, methylenedioxyphenyl, perfluorinated methyl, or perfluorinated ethyl. In other embodiments, R$^4$ is methyl, ethyl, C$_3$ alkyl, n-propyl, isopropyl, ethoxy, methoxy, 5-hydroxy pyridyl, 5-hydroxy pyrid-3-yl, indolyl, 1-indolyl, 1,2,3,4-tetrahydroisoquinolyl, 2-1,2,3,4-tetrahydroisoquinolyl, furyl, 2-furyl), 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, benzyl, pyridyl, 3-pyridyl, methylenedioxyphenyl, perfluorinated methyl, or perfluorinated ethyl. In some embodiments, R$^5$ is H, halogen, —CN, hydroxy (—OH), methanoyl (—COH), carboxy (—CO$_2$H), C$_1$-C$_7$ alkyl, C$_1$-C$_6$ alkoxy, cycloalkyl, heterocyclyl, aryl, or heteroaryl, which methanoyl (—COH), carboxy (—CO$_2$H), C$_1$-C$_7$ alkyl, C$_1$-C$_6$ alkoxy, cycloalkyl, heterocyclyl, aryl, or heteroaryl is optionally substituted with one or more of halogen, oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, —CONH$_2$, —CON(CH$_3$)$_2$, C$_1$-C$_3$ alkyl, C$_1$-C$_3$ perfluorinated alkyl, or C$_1$-C$_3$ alkoxy. In other embodiments, R$^5$ is phenyl, 5-hydroxy pyridyl, 5-hydroxy pyrid-3-yl, 6-hydroxy pyridyl, 6-hydroxy pyrid-3-yl, 4-hydroxy pyridyl, 4-hydroxy pyrid-3-yl, indolyl, 1-indolyl, 1,2,3,4-tetrahydroisoquinolyl, 2-1,2,3,4-tetrahydroisoquinolyl, 1,2-methylenedioxyphenyl, 2,3-methylenedioxyphenyl, —CO-morpholin-4-yl, —CON(CH$_3$)$_2$, Cl, hydroxy (—OH), methyl, C$_{1-5}$ alkyl, C$_3$ alkyl, n-propyl, isopropyl, —CN, ethynyl, —CONH$_2$, —CON(CH$_3$)$_2$, 2-(morpholinyl)ethoxy, ethoxy, methoxy, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, perfluorinated methyl, or perfluorinated ethyl. In still other embodiments, R$^5$ is phenyl, 5-hydroxy pyridyl, 5-hydroxy pyrid-3-yl, indolyl, 1-indolyl, 1,2,3,4-tetrahydroisoquinolyl, 2-1,2,3,4-tetrahydroisoquinolyl, 1,2-methylenedioxyphenyl, 2,3-methylenedioxyphenyl, methyl, C$_3$ alkyl, n-propyl, isopropyl, ethoxy, methoxy, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, perfluorinated methyl, or perfluorinated ethyl. In yet other embodiments, R$^5$ is phenyl, 5-hydroxy pyridyl, 5-hydroxy pyrid-3-yl, indolyl, 1-indolyl, 1,2,3,4-tetrahydroisoquinolyl, 2-1,2,3,4-tetrahydroisoquinolyl, 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, or 3,5-bis-trifluoromethyl phenyl. In some embodiments, X is

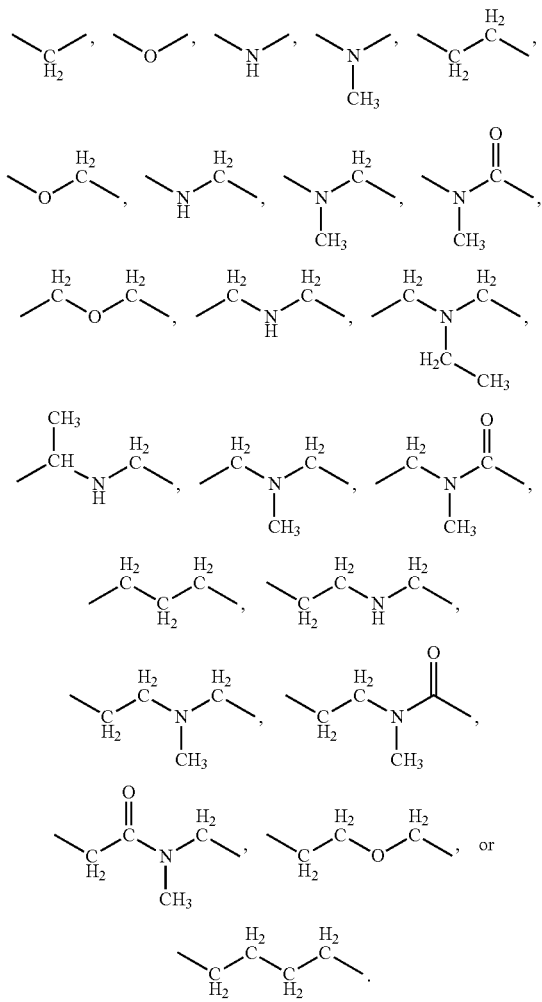

In yet other embodiments, X is

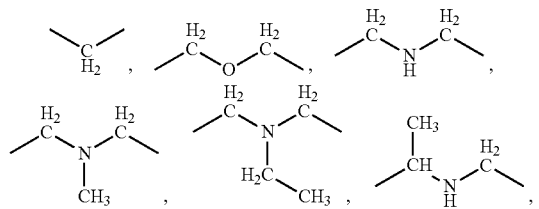

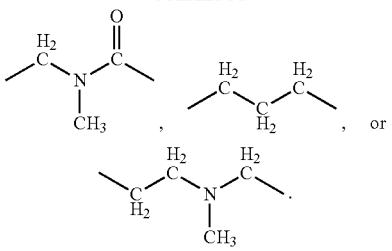

In some embodiments, ring A is

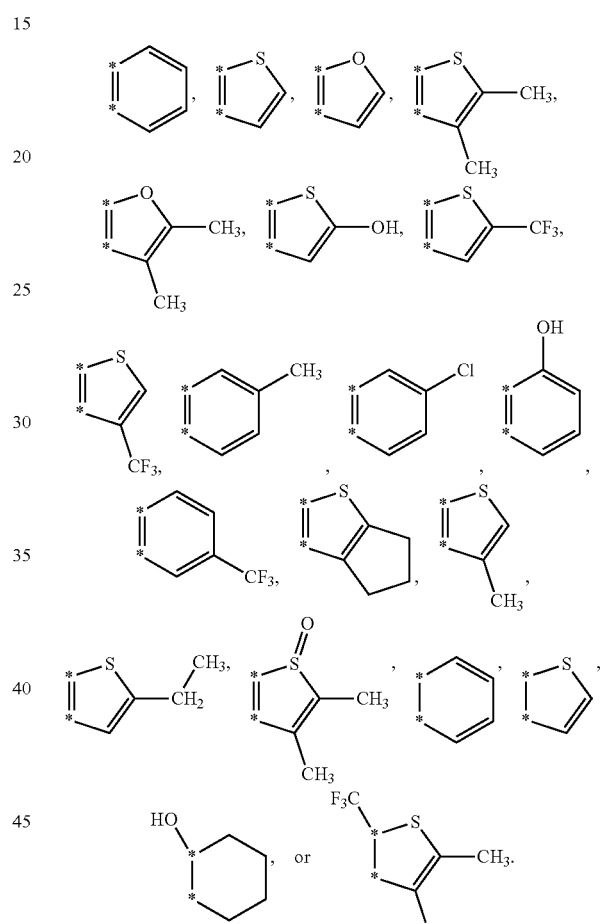

In other embodiments, ring A is

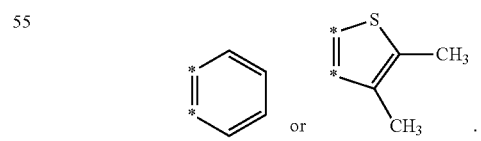

In some embodiments, Formula (I) is I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, or I-54. In other embodiments, $R^1$ is not H, $R^2$ is not H, $R^3$ is not H, $R^4$ is not 3-methoxyphenyl, $R^5$ is not 3-methoxyphenyl, X is not

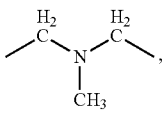

or ring A is not

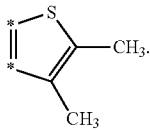

In certain embodiments, compound I-1 is excluded from Formula (I).

Some embodiments of the invention include a composition comprising a compound, as disclosed herein (e.g., Formula (I)). In certain embodiments, the amount of the compound is from about 0.0001% (by weight total composition) to about 99%. In other embodiments, the composition further comprises a formulary ingredient, an adjuvant, or a carrier.

Some embodiments of the invention include a pharmaceutical composition comprising a compound, as disclosed herein (e.g., Formula (I)). In some embodiments, the amount of the compound is from about 0.0001% (by weight total composition) to about 50%. In other embodiments, the pharmaceutical composition further comprises a formulary ingredient, an adjuvant, or a carrier.

Some embodiments of the invention include a method for providing an animal with a compound comprising one or more administrations of one or more compositions comprising a compound as disclosed herein (e.g., Formula (I)), where the compositions may be the same or different if there is more than one administration. In other embodiments, at least one of the one or more compositions further comprises a formulary ingredient. In certain embodiments, at least one of the one or more compositions comprises a composition as disclosed herein or a pharmaceutical composition as disclosed herein. In still other embodiments, at least one of the one or more administrations comprises parenteral administration, a mucosal administration, intravenous administration, subcutaneous administration, topical administration, intradermal administration, oral administration, sublingual administration, intranasal administration, or intramuscular administration. In other embodiments, if there is more than one administration at least one composition used for at least one administration is different from the composition of at least one other administration. In certain embodiments, the compound of at least one of the one or more compositions is administered to the animal in an amount of from about 0.01 mg/kg animal body weight to about 15 mg/kg animal body weight. In yet still other embodiments, the animal is a human, a rodent, or a primate.

Some embodiments of the invention include a method for treating an animal for a disease, comprising one or more administrations of one or more compositions comprising a compound as disclosed here (e.g., Formula (I)), where the compositions may be the same or different if there is more than one administration. In some embodiments, at least one of the one or more compositions further comprises a formulary ingredient. In other embodiments, at least one of the one or more compositions comprises a composition as disclosed herein or a pharmaceutical composition as disclosed herein. In yet other embodiments, at least one of the one or more administrations comprises parenteral administration, a mucosal administration, intravenous administration, subcutaneous administration, topical administration, intradermal administration, oral administration, sublingual administration, intranasal administration, or intramuscular administration. In still other embodiments, if there is more than one administration at least one composition used for at least one administration is different from the composition of at least one other administration. In other embodiments, the compound of at least one of the one or more compositions is administered to the animal in an amount of from about 0.005 mg/kg animal body weight to about 50 mg/kg animal body weight. In some embodiments, the animal is a human, a rodent, or a primate. In certain embodiments, the animal is in need of the treatment. In other embodiments, the method is for treating cancer. In yet other embodiments, the method is for treating pancreatic cancer, pancreatic ductal adenocarcinoma, lung cancer, liver cancer, colorectal cancer, colon cancer, rectal cancer, melanoma, cutaneous malignant melanoma, melanoma tumorigenesis, bladder cancer, prostate cancer, malignant nerve sheath tumors, multiple myeloma, breast cancer, squamous cell carcinoma, head and neck squamous cell carcinoma, lymphoma, leukemia, bone marrow cancer, non-Hodgkin lymphoma, diffuse large B-cell lymphoma, glioblastoma multiforme, endometrial cancer, kidney cancer, basal cell carcinoma, thyroid cancer, neuroblastoma, ovarian cancer, renal cell carcinoma, hepatocellular carcinoma, chronic lymphocytic leukemia (CLL), acute lymphoblastic leukemia, rhabdomyosarcoma, meningioma, gastric cancer, Glioma, oral cancer, nasopharyngeal carcinoma, stomach cancer, uterine cancer, medulloblastoma, cancers that can result in metastasis, cancers resulting from metastasis, or cancerous tumors thereof. In yet other embodiments, the method is for treating pancreatic cancer, pancreatic ductal adenocarcinoma, lung cancer, liver cancer, colorectal cancer, colon cancer, rectal cancer, melanoma, cutaneous malignant melanoma, melanoma tumorigenesis, bladder cancer, malignant nerve sheath tumors, multiple myeloma, breast cancer, squamous cell carcinoma, head and neck squamous cell carcinoma, ovarian cancer, prostate cancer, medulloblastoma, cancers that can result in metastasis, cancers resulting from metastasis, or cancerous tumors thereof. In certain embodiments, the method is for treating pancreatic cancer, pancreatic ductal adenocarcinoma, lung cancer, liver cancer, ovarian cancer, prostate cancer, medulloblastoma, cancers that can result in metastasis, cancer resulting from metastasis of pancreatic cancer, lung cancer resulting from metastasis, or cancerous tumors thereof.

Some embodiments of the invention include a method for preparing a compound as disclosed herein (e.g., Formula (I)) comprising,
(a) reacting a compound of Formula (II) with a compound of Formula (III) to result in a mixture comprising a compound of Formula (IV);
(b) reacting a compound of Formula (IV) with a suitable compound to convert an oxo to a halogen to result in a mixture comprising a compound of Formula (V);
(c) reacting a compound of Formula (V) with a compound of Formula (VI); and;
(d) recovering Formula (I), where Formula (II) is

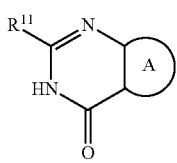

(II)

and $R^{11}$ is a halogen or —CH$_2$-halogen;
Formula (III) is $R^5$—X—H (III);
Formula (IV) is

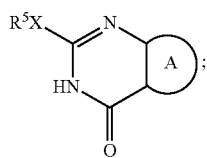

(IV)

Formula (V) is

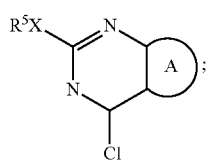

(V)

and
Formula (VI) is

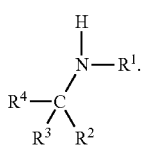

(VI)

In some embodiments, $R^{11}$ is —CH$_2$-halogen, —CH$_2$Br, or —CH$_2$Cl. In other embodiments, the suitable compound to convert an oxo to a halogen is POCl$_3$ or POBr$_3$.

Other embodiments of the invention are also discussed herein.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

FIG. 1: Effects of some compounds of Formula (I) on soft agar growth and normal growth in 2D of pancreatic carcinoma cell lines.

FIG. 2: Inhibition of multiple RalGEFs can have a synergistic inhibitory effect on growth in agar of pancreatic carcinoma cells.

FIG. 3: Some compounds of Formula (I) can be a pan-RalGEF inhibitor. HEK-293 cells were co-transfected with HA-activated K-Ras and GFP-RalGDS (FIG. 3A) or RGL2 (FIG. 3B) in the presence of some compounds. The cells were lysed. A compound to be tested was added to the lysate to a final concentration 10 μM, which was then incubated with anti-GFP-beads overnight. The immunoprecipitate (IP) was then analysed for the presence of Ras by immunoblot (IB).

FIG. 6: Some compounds of Formula (I) suppress pancreatic cancer cell metastasis. NRG mice were sub-cutaneously inoculated with PBS ("no tumor cells") or 5×10$^6$ Ras driven Mia-PaCa-2 cells. Mice were allowed to recover for 1 week and then injected (ip) with PBS/DMSO carrier or 10 mg/kg of compound I-1 every other day for 2 weeks. One week later, mice were scored for primary tumor growth and lung metastasis.

DETAILED DESCRIPTION

Figure 1A:
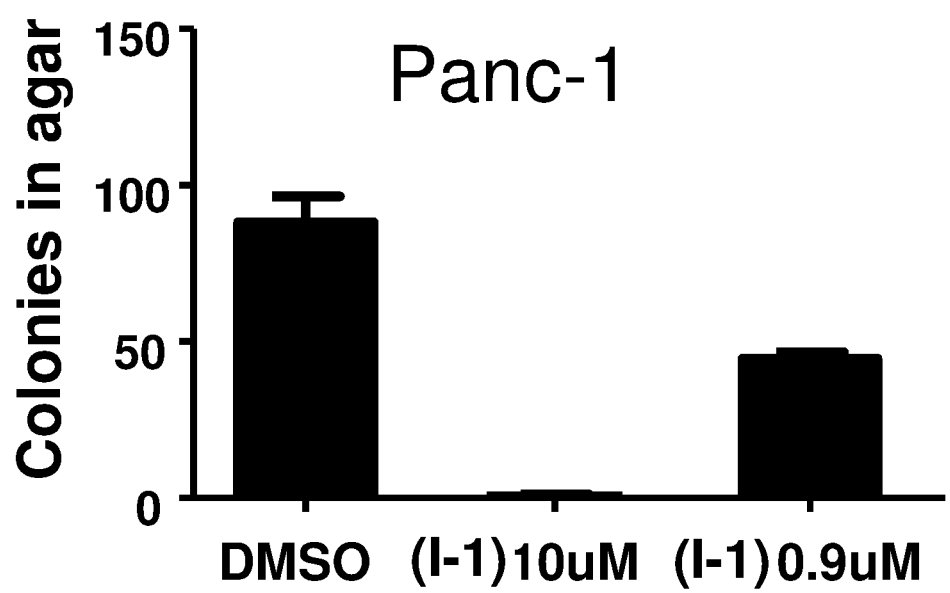
FIGS. 1A and 1B: Panc-1 (FIG. 1A) and MiaPaCa-2 (FIG. 1B) mutant Ras containing pancreatic tumor cell lines were plated in soft agar in the presence of 10 μM or 0.9 μM of compound I-1 and scored for the formation of colonies.

While embodiments encompassing the general inventive concepts may take diverse forms, various embodiments will be described herein, with the understanding that the present disclosure is to be considered merely exemplary, and the general inventive concepts are not intended to be limited to the disclosed embodiments.

Some embodiments of the invention include inventive compounds (e.g., compounds of Formula (I)). Other embodiments include compositions (e.g., pharmaceutical compositions) comprising the inventive compound. Still other embodiments of the invention include compositions for treating, for example, certain diseases using the inventive compounds. Some embodiments include methods of using the inventive compound (e.g., in compositions or in pharmaceutical compositions) for administering and treating. Further embodiments include methods for making the inventive compound.

As used herein (unless otherwise specified), the term "alkyl" means a monovalent, straight or branched hydrocarbon chain. For example, the terms "$C_1$-$C_7$ alkyl" or "$C_1$-$C_4$ alkyl" refer to straight- or branched-chain saturated hydrocarbon groups having from 1 to 7 (e.g., 1, 2, 3, 4, 5, 6, or 7), or 1 to 4 (e.g., 1, 2, 3, or 4), carbon atoms, respectively. Examples of $C_1$-$C_7$ alkyl groups include, but are not limited to, methyl, ethyl, n-propyl, i-propyl, n-butyl, s-butyl, t-butyl, n-pentyl, s-pentyl, n-hexyl, and n-septyl. Examples of $C_1$-$C_4$ alkyl groups include, but are not limited to, methyl, ethyl, n-propyl, i-propyl, n-butyl, s-butyl, and t-butyl.

As used herein (unless otherwise specified), the term "alkenyl" means a monovalent, straight or branched hydrocarbon chain that includes one or more (e.g., 1, 2, 3, or 4) double bonds. Examples of alkenyl groups include, but are not limited to, vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, and 5-hexenyl.

As used herein (unless otherwise specified), the term "alkoxy" means any of the above alkyl groups which is attached to the remainder of the molecule by an oxygen atom (alkyl-O—). Examples of alkoxy groups include, but are not limited to, methoxy (sometimes shown as MeO—), ethoxy, isopropoxy, propoxy, and butyloxy.

As used herein (unless otherwise specified), the term "alkynyl" means a monovalent, straight or branched hydrocarbon chain that includes one or more (e.g., 1, 2, 3, or 4) triple bonds and that also may optionally include one or more (e.g. 1, 2, 3, or 4) double bonds in the chain. Examples of alkynyl groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

As used herein (unless otherwise specified), the term "aryl" means a monovalent, monocyclic or bicyclic, 5, 6, 7, 8, 9, 10, 11, or 12 member aromatic hydrocarbon group which, when unsubstituted. Examples of aryl groups include, but are not limited to, phenyl, naphthyl, tolyl, and xylyl. For an bicyclic aryl that is designated as substituted, one or both rings can be substituted.

As used herein (unless otherwise specified), the term "cycloalkyl" means a monovalent, monocyclic or bicyclic, 3, 4, 5, 6, 7, 8, 9, 10, 11, or 12 membered hydrocarbon group. The rings can be saturated or partially unsaturated. Examples of cycloalkyl groups include, but are not limited to, cyclopropyl, cyclobutyl, cyclopentyl, cyclohexyl, cycloheptyl, cyclooctyl, and bicycloalkyls (e.g., bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds). For a monocyclic cycloalkyl, the ring is not aromatic. For a bicyclic cycloalkyl, if one ring is aromatic, then the other is not aromatic. For a bicyclic cycloalkyl that is designated as substituted, one or both rings can be substituted.

As used herein (unless otherwise specified), the term "halogen" means monovalent Cl, F, Br, or I.

As used herein (unless otherwise specified), the term "heteroaryl" means a monovalent, monocyclic or bicyclic, 5, 6, 7, 8, 9, 10, 11, or 12 membered, hydrocarbon group, where 1, 2, 3, 4, 5, or 6 carbon atoms are replaced by a hetero atom independently selected from nitrogen, oxygen, or sulfur atom, and the monocyclic or bicyclic ring system is aromatic. Examples of heteroaryl groups include, but are not limited to, thienyl (or thiophenyl), furyl, indolyl, pyrrolyl, pyridinyl, pyrazinyl, oxazolyl, thiaxolyl, quinolinyl, pyrimidinyl, imidazolyl, triazolyl, tetrazolyl, 1H-pyrazol-4-yl, 1-Me-pyrazol-4-yl, pyridin-3-yl, pyridin-4-yl, 3,5-dimethylisoxazolyl, 1H-pyrrol-3-yl, 3,5-di-Me-pyrazolyl, and 1H-pyrazol-4-yl. For a bicyclic heteroaryl, if one ring is aryl, then the other is heteroaryl. For a bicyclic heteroaryl, one or both rings can have one or more hetero atoms. For a bicyclic heteroaryl that is designated as substituted, one or both rings can be substituted.

As used herein (unless otherwise specified), the term "heterocyclyl" means a monovalent, monocyclic or bicyclic, 5, 6, 7, 8, 9, 10, 11, or 12 membered, hydrocarbon, where 1, 2, 3, 4, 5, or 6 carbon atoms are replaced by a hetero atom independently selected from nitrogen atom, oxygen atom, or sulfur atom, and the monocyclic or bicyclic ring system is not aromatic. Examples of heterocyclyl groups include, but are not limited to, tetrahydropyran, pyrolidinyl (e.g., pyrrolidin-1-yl, pyrrolidin-2-yl, pyrrolidin-3-yl, or pyrrolidin-4-yl), piperazinyl (e.g., piperazin-1-yl, piperazin-2-yl, piperazin-3-yl, or piperazin-4-yl), piperidinyl (e.g., piperadin-1-yl, piperadin-2-yl, piperadin-3-yl, or piperadin-4-yl), and morpholinyl (e.g., morpholin-1-yl, morpholin-2-yl, morpholin-3-yl, or morpholin-4-yl). For a bicyclic heterocyclyl, if one ring is aromatic (e.g., monocyclic aryl or heteroaryl), then the other ring is not aromatic. For a bicyclic heterocyclyl, one or both rings can have one or more hetero atoms. For a bicyclic heterocyclyl that is designated as substituted, one or both rings can be substituted.

As used herein (unless otherwise specified), the term "hetero atom" means an atom selected from nitrogen atom, oxygen atom, or sulfur atom.

As used herein (unless otherwise specified), the terms "hydroxy" or "hydroxyl" indicates the presence of a monovalent —OH group.

As used herein (unless otherwise specified), the term "substituted" (e.g., as in substituted alkyl) means that one or more hydrogen atoms of a chemical group (with one or more hydrogen atoms) can be replaced by one or more non-hydrogen substituents selected from the specified options. The replacement can occur at one or more positions. The term "optionally substituted" means that one or more hydrogen atoms of a chemical group (with one or more hydrogen atoms) can be, but is not required to be substituted.

Some compounds of the invention can have one or more chiral centers and can exist in and be isolated in optically active and racemic forms, for any of the one or more chiral centers. Some compounds can exhibit polymorphism. The compounds of the present invention (e.g., Formula I) encompass any optically active, racemate, stereoisomer form, polymorphism, or mixtures thereof. If a chiral center does not provide an indication of its configuration (i.e., R or S) in a chemical structure, it should be considered to represent R, S or a racemate.

Compounds and Compositions Including
Pharmaceutical Compositions

Some embodiments of the invention include compounds of Formula (I):

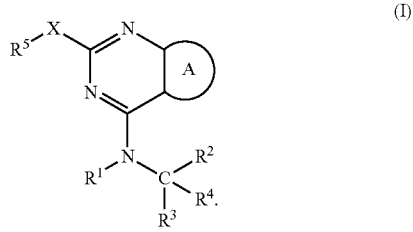

In other embodiments, $R^1$ can be monovalent H, $C_1$-$C_3$ alkyl (e.g., $C_1$, $C_2$, or $C_3$ alkyl), $C_2$-$C_3$ alkenyl (e.g., $C_2$ or $C_3$ alkenyl), or $C_2$-$C_3$ alkynyl (e.g., $C_2$ or $C_3$ alkynyl), which $C_1$-$C_3$ alkyl, $C_2$-$C_3$ alkenyl, or $C_2$-$C_3$ alkynyl can optionally be substituted with one or more (e.g., 0, 1, 2, 3, 4, 5, or 6) of halogen (e.g., F, Cl, Br, or I), hydroxy (—OH), methanoyl (—COH), carboxy (—CO$_2$H), ethynyl (—CCH), cyano (—CN), sulfo (—SO$_3$H), methyl, or ethyl. In other embodiments, $R^1$ can be H or $C_1$-$C_3$ alkyl (e.g., $C_1$, $C_2$, or $C_3$ alkyl), which $C_1$-$C_3$ alkyl can optionally be substituted with one or more (e.g., 0, 1, 2, 3, 4, 5, or 6) of halogen (e.g., F, Cl, Br, or I), hydroxy (—OH), methanoyl (—COH), carboxy (—CO$_2$H), cyano (—CN), ethynyl (—CCH), sulfo (—SO$_3$H), methyl, or ethyl. In some embodiments, $R^1$ can be H, methyl, ethyl, perfluorinated methyl, or perfluorinated ethyl.

In other embodiments, $R^2$ can be monovalent H, halogen (e.g., F, Cl, Br, or I), hydroxy (—OH), cyano (—CN), sulfo (—SO$_3$H), $C_1$-$C_3$ alkyl (e.g., $C_1$, $C_2$, or $C_3$ alkyl), $C_2$-$C_3$ alkenyl (e.g., $C_2$ or $C_3$ alkenyl), $C_2$-$C_3$ alkynyl (e.g., $C_2$ or $C_3$ alkynyl), or $C_1$-$C_2$ alkoxy (e.g., $C_1$ or $C_2$ alkoxy), which $C_1$-$C_3$ alkyl, $C_2$-$C_3$ alkenyl, $C_2$-$C_3$ alkynyl, or $C_1$-$C_2$ alkoxy can optionally be substituted with one or more (e.g., 0, 1, 2, 3, 4, 5, or 6) of halogen (e.g., F, Cl, Br, or I), hydroxy (—OH), methanoyl (—COH), carboxy (—CO$_2$H), ethynyl (—CCH), cyano (—CN), sulfo (—SO$_3$H), methyl, or ethyl. In other embodiments, $R^2$ can be monovalent H, halogen (e.g., F, Cl, Br, or I), hydroxy (—OH), $C_1$-$C_3$ alkyl (e.g., $C_1$, $C_2$, or $C_3$ alkyl), or $C_1$-$C_2$ alkoxy (e.g., $C_1$ or $C_2$ alkoxy), which $C_1$-$C_3$ alkyl or $C_1$-$C_2$ alkoxy can optionally be substituted with one or more (e.g., 0, 1, 2, 3, 4, 5, or 6) of halogen (e.g., F, Cl, Br, or I), hydroxy (—OH), methanoyl (—COH), carboxy (—CO$_2$H), cyano (—CN), ethynyl (—CCH), sulfo (—SO$_3$H), methyl, or ethyl. In some embodiments, $R^2$ can be H, halogen (e.g., F, Cl, Br, or I), hydroxy (—OH), cyano (—CN), sulfo (—SO$_3$H), methyl, ethyl, methoxy, perfluorinated methyl, or perfluorinated ethyl.

In other embodiments, $R^3$ can be monovalent H, halogen (e.g., F, Cl, Br, or I), hydroxy (—OH), cyano (—CN), sulfo (—SO$_3$H), $C_1$-$C_3$ alkyl (e.g., $C_1$, $C_2$, or $C_3$ alkyl), $C_2$-$C_3$ alkenyl (e.g., $C_2$ or $C_3$ alkenyl), $C_2$-$C_3$ alkynyl (e.g., $C_2$ or $C_3$ alkynyl), or $C_1$-$C_2$ alkoxy (e.g., $C_1$ or $C_2$ alkoxy), which $C_1$-$C_3$ alkyl, $C_2$-$C_3$ alkenyl, $C_2$-$C_3$ alkynyl, or $C_1$-$C_2$ alkoxy can optionally be substituted with one or more (e.g., 0, 1, 2, 3, 4, 5, or 6) of halogen (e.g., F, Cl, Br, or I), hydroxy (—OH), methanoyl (—COH), carboxy (—CO$_2$H), ethynyl (—CCH), cyano (—CN), sulfo (—SO$_3$H), methyl, or ethyl. In other embodiments, $R^3$ can be monovalent H, halogen (e.g., F, Cl, Br, or I), hydroxy (—OH), $C_1$-$C_3$ alkyl (e.g., $C_1$, $C_2$, or $C_3$ alkyl), or $C_1$-$C_2$ alkoxy (e.g., $C_1$ or $C_2$ alkoxy), which $C_1$-$C_3$ alkyl or $C_1$-$C_2$ alkoxy can optionally be substituted with one or more (e.g., 0, 1, 2, 3, 4, 5, or 6) of halogen (e.g., F, Cl, Br, or I), hydroxy (—OH), methanoyl (—COH), carboxy (—CO$_2$H), cyano (—CN), ethynyl (—CCH), sulfo (—SO$_3$H), methyl, or ethyl. In some embodiments, $R^3$ can be H, halogen (e.g., F, Cl, Br, or I), hydroxy (—OH), cyano (—CN), sulfo (—SO$_3$H), methyl, ethyl, methoxy, perfluorinated methyl, or perfluorinated ethyl.

In some embodiments, $R^4$ can be monovalent H, halogen (e.g., F, Cl, Br, or I), —CN, hydroxy (—OH), methanoyl (—COH), carboxy (—CO$_2$H), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), $C_1$-$C_6$ alkoxy (e.g., $C_1$, $C_2$, $C_3$, $C_4$, $C_5$, or $C_6$ alkoxy), cycloalkyl, heterocyclyl, aryl, or heteroaryl, which methanoyl (—COH), carboxy (—CO$_2$H), $C_1$-$C_7$ alkyl, $C_2$-$C_7$ alkenyl, $C_2$-$C_7$ alkynyl, $C_1$-$C_6$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, or $C_1$-$C_3$ alkoxy. In other embodiments, $R^4$ can be monovalent H, halogen (e.g., F, Cl, Br, or I), —CN, hydroxy (—OH), methanoyl (—COH), carboxy (—CO$_2$H), $C_1$-$C_7$ alkyl (e.g., $C_1$, $C_2$, $C_3$, $C_4$, $C_5$, $C_6$, or $C_7$ alkyl), $C_1$-$C_6$ alkoxy (e.g., $C_1$, $C_2$, $C_3$, $C_4$, $C_5$, or $C_6$ alkoxy), cycloalkyl, heterocyclyl, aryl, or heteroaryl, which methanoyl (—COH), carboxy (—CO$_2$H), $C_1$-$C_7$ alkyl, $C_1$-$C_6$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, or $C_1$-$C_3$ alkoxy. In some embodiments, $R^4$ can be Cl, hydroxy (—OH), methyl, ethyl, $C_{1-5}$ alkyl, $C_3$ alkyl (e.g., n-propyl or isopropyl), —CN, ethynyl, —CONH$_2$, —CON(CH$_3$)$_2$, 2-(morpholinyl)ethoxy, —CO-morpholin-4-yl, ethoxy, methoxy, 5-hydroxy pyridyl (5-hydroxy pyrid-3-yl), indolyl (e.g., 1-indolyl), 1,2,3,4-tetrahydroisoquinolyl (e.g., 2-1,2,3,4-tetrahydroisoquinolyl), 1,2-methylenedioxyphenyl, 2,3-methylenedioxyphenyl, furyl (e.g., 2-furyl), 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, benzyl, pyridyl, 3-pyridyl, methylenedioxyphenyl, perfluorinated methyl, or perfluorinated ethyl. In some embodiments, $R^4$ can be methyl, ethyl, $C_3$ alkyl, n-propyl, isopropyl, ethoxy, methoxy, 5-hydroxy pyridyl (e.g., 5-hydroxy pyrid-3-yl), indolyl (e.g., 1-indolyl), 1,2,3,4-tetrahydroisoquinolyl (e.g., 2-1,2,3,4-tetrahydroisoquinolyl), furyl (e.g., 2-furyl), 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, benzyl, pyridyl, 3-pyridyl, methylenedioxyphenyl, perfluorinated methyl, or perfluorinated ethyl.

In some embodiments, $R^5$ can be monovalent H, halogen (e.g., F, Cl, Br, or I), —CN, hydroxy (—OH), methanoyl (—COH), carboxy (—CO$_2$H), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), $C_1$-$C_6$ alkoxy (e.g., $C_1$, $C_2$, $C_3$, $C_4$, $C_5$, or $C_6$ alkoxy), cycloalkyl, heterocyclyl, aryl, or heteroaryl, which methanoyl (—COH), carboxy (—CO$_2$H), $C_1$-$C_7$ alkyl, $C_2$-$C_7$ alkenyl, $C_2$-$C_7$ alkynyl, $C_1$-$C_6$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, —CONH$_2$, —CON(CH$_3$)$_2$, $C_1$-$C_3$ alkyl, $C_1$-$C_3$ perfluorinated alkyl, or $C_1$-$C_3$ alkoxy. In other embodiments, $R^5$ can be monovalent H, halogen (e.g., F, Cl, Br, or I), —CN, hydroxy (—OH), methanoyl (—COH), carboxy (—CO$_2$H), $C_1$-$C_7$ alkyl (e.g., $C_1$, $C_2$, $C_3$, $C_4$, $C_5$, $C_6$, or $C_7$ alkyl), $C_1$-$C_6$ alkoxy (e.g., $C_1$, $C_2$, $C_3$, $C_4$, $C_5$, or $C_6$ alkoxy), cycloalkyl, heterocyclyl, aryl, or heteroaryl, which methanoyl (—COH), carboxy (—CO$_2$H), $C_1$-$C_7$ alkyl, $C_1$-$C_6$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, —CONH$_2$, —CON(CH$_3$)$_2$, $C_1$-$C_3$ alkyl, $C_1$-$C_3$ perfluorinated alkyl, or $C_1$-$C_3$ alkoxy. In some embodiments, $R^5$ can be phenyl, 5-hydroxy pyridyl (e.g., 5-hydroxy pyrid-3-yl), 6-hydroxy pyridyl (e.g., 6-hydroxy pyrid-3-yl), 4-hydroxy pyridyl (e.g., 4-hydroxy pyrid-3-yl), indolyl (e.g., 1-indolyl), 1,2,3,4-tetrahydroisoquinolyl (e.g., 2-1,2,3,4-tetrahydroisoquinolyl), 1,2-methylenedioxyphenyl, 2,3-methylenedioxyphenyl, —CO-morpholin-4-yl, —CON(CH$_3$)$_2$, Cl, hydroxy (—OH), methyl, ethyl, $C_{1-5}$ alkyl, $C_3$ alkyl (e.g., n-propyl or isopropyl), —CN, ethynyl, —CONH$_2$, —CON(CH$_3$)$_2$, 2-(morpholinyl)ethoxy, ethoxy, methoxy, furyl (e.g., 2-furyl), 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, perfluorinated methyl, or perfluorinated ethyl. In some embodiments, $R^5$ can be phenyl, 5-hydroxy pyridyl (e.g., 5-hydroxy pyrid-3-yl), indolyl (e.g., 1-indolyl), 1,2,3,4-tetrahydroisoquinolyl (e.g., 2-1,2,3,4-tetrahydroisoquinolyl), furyl (e.g., 2-furyl), 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, or 3,5-bis-trifluoromethyl phenyl.

In some embodiments, X can be a bivalent $C_1$-$C_7$ alkyl (e.g., $C_1$, $C_2$, $C_3$, $C_4$, $C_5$, $C_6$, or $C_7$ alkyl) where 1, 2, or 3 of the $C_1$-$C_7$ alkyl carbons can be optionally replaced with a hetero atom (e.g., N, O, or S) which can be the same or different if more than one carbon atom is replaced, and which $C_1$-$C_7$ alkyl (e.g., including any of the hetero atom replacements, as chemically appropriate) can optionally be substituted with one or more (e.g., 0, 1, 2, 3, 4, 5, or 6) of halogen (e.g., F, Cl, Br, or I), oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, —CONH$_2$, —CON(CH$_3$)$_2$, $C_1$-$C_3$ alkyl, $C_1$-$C_3$ perfluorinated alkyl, or $C_1$-$C_3$ alkoxy. In other embodiments, X can be a bivalent $C_1$-$C_4$ alkyl (e.g., $C_1$, $C_2$, $C_3$, or $C_4$ alkyl) where 1, 2, or 3 of the $C_1$-$C_4$ alkyl carbons can be optionally replaced with a hetero atom (e.g., N, O, or S), and which $C_1$-$C_4$ alkyl (e.g., including any of the hetero atom replacements, as chemically appropriate) can optionally be substituted with one or more (e.g., 0, 1, 2, 3, 4, 5, or 6) of halogen (e.g., F, Cl, Br, or I), oxo (═O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, —CONH$_2$, —CON(CH$_3$)$_2$, $C_1$-$C_3$ alkyl, $C_1$-$C_3$ perfluorinated alkyl, or $C_1$-$C_3$ alkoxy. In some embodiments, X can be

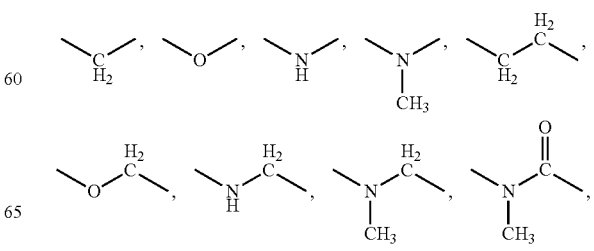

-continued

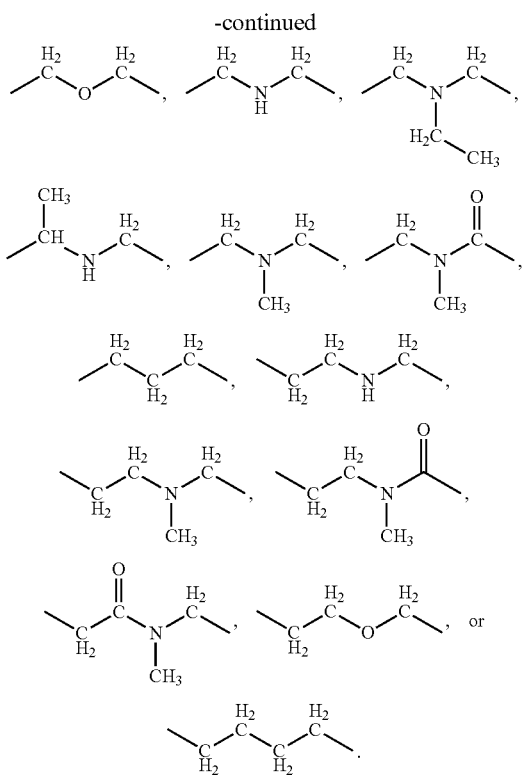

In some embodiments, X can be

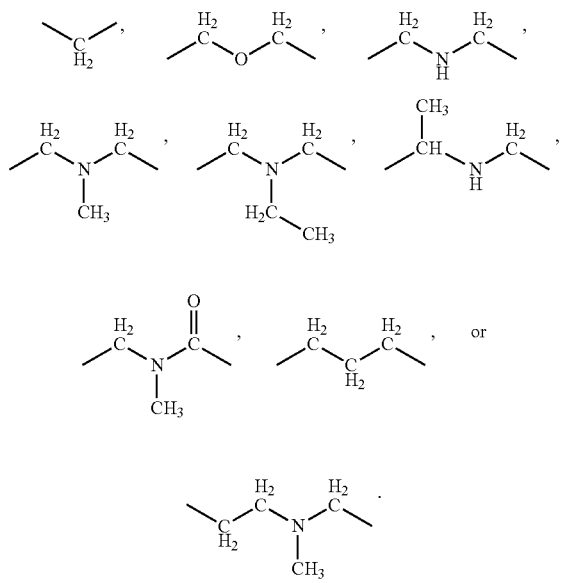

In certain embodiments, X can be

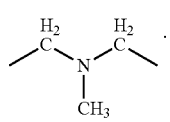

Any of the above X moieties can be inserted into the structure as shown or can be rotated 180 degrees along a vertical axis and then inserted into the structure (e.g.,

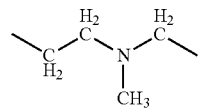

can be rotated 180 degrees along a vertical axis to

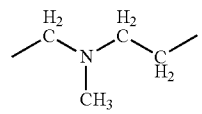

and then inserted into the structure).

In some embodiments, ring A is a monocyclic or bicyclic ring comprising 4, 5, 6, 7, 8, 9, or 10 carbon atoms (e.g., 4, 5, 6, 7, or 8 carbon atoms), where 1, 2, 3, 4, or 5 (e.g., 1, 2, or 3) of the non-fusion carbon atoms, can be optionally replaced with a hetero atom (e.g., N, O, S) and the hetero atom can be the same or different if more than one carbon atom is replaced, which ring A carbon atoms or any of the hetero atom replacements (as chemically appropriate) can optionally be substituted with one or more (e.g., 0, 1, 2, 3, 4, 5, or 6) of halogen (e.g., F, Cl, Br, or I), oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, —CONH$_2$, —CON(CH$_3$)$_2$, C$_1$-C$_6$ alkyl, C$_1$-C$_6$ perfluoronated alkyl (e.g., trifluoromethyl or perfluoroethyl), or C$_1$-C$_5$ alkoxy. The two "fusion carbon atoms" are defined as the two ring A carbon atoms which fuse ring A to the pyrimidine-like moiety; "non-fusion carbon atoms" are defined as the other carbon atoms in ring A that are not the two fusion carbon atoms. Ring A can be monocyclic or bicyclic, to create (i.e., together with the pyrimidine-like moiety) a bicyclic or tricyclic structure, respectively. Ring A can, in certain embodiments, comprise 1, 2, 3, 4, or 5 double bonds, which can be in one or both rings if Ring A is bicyclic. In other embodiments, ring A can itself be aromatic, can create an aromatic of the bi- or tri-cyclic (i.e., ring A fused with the pyrimidine-like moiety), or both. In certain embodiments, the fusion carbon atoms can be single bonded or double bonded to each other. In some embodiments, ring A can be

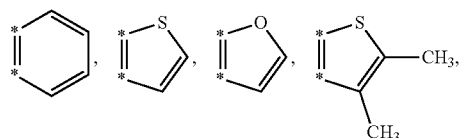

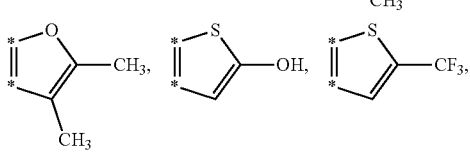

-continued

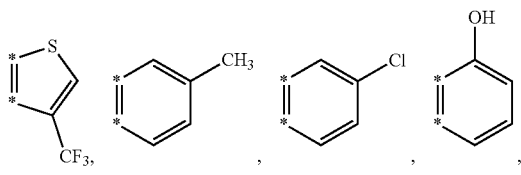

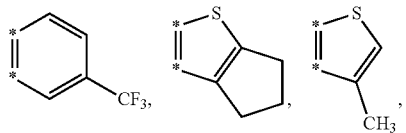

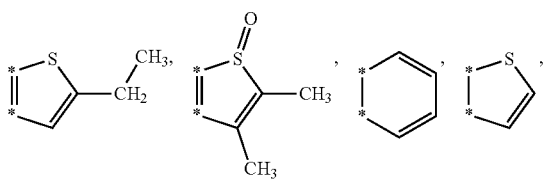

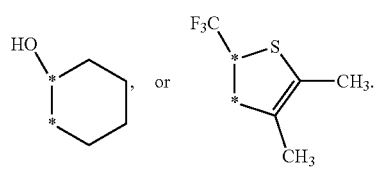

In some embodiments, ring A can be

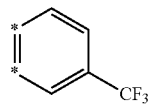

As used herein, * is defined to indicate a point of fusion for each of the two fusion carbon atoms of ring A. Any of the above moieties can be inserted into the structure as shown or can be rotated 180 degrees along a horizontal axis and then inserted into the structure (e.g.,

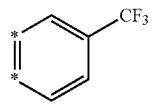 [SMILES: FC(F)(F)c1c*:*cc1]

can be rotated 180 degrees along a horizontal axis to

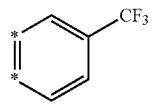 [SMILES: FC(F)(F)c1c*:*cc1]

and then inserted into the structure).

In some embodiments, the compounds of Formula (I) can be selected from those specified in Table 1.

TABLE 1

| Compound Number | Structure |
|---|---|
| I-1 | 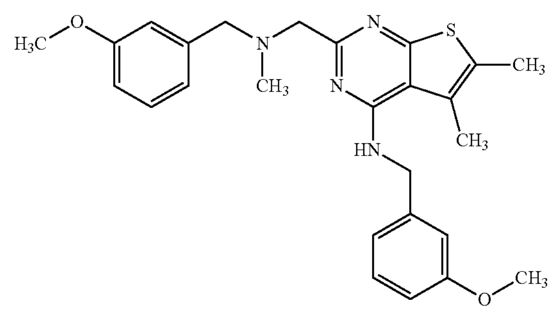 |
| I-2 | 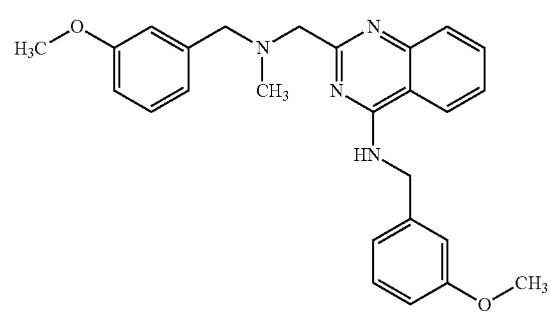 |

TABLE 1-continued

| Compound Number | Structure |
| --- | --- |
| I-3 | (structure) |
| I-4 | (structure) |
| I-5 | (structure) |
| I-6 | (structure) |

TABLE 1-continued

| Compound Number | Structure |
| --- | --- |
| I-7 | *(chemical structure)* |
| I-8 | *(chemical structure)* |
| I-9 | *(chemical structure)* |
| I-10 | *(chemical structure)* |

TABLE 1-continued

| Compound Number | Structure |
| --- | --- |
| I-11 | *(chemical structure)* |
| I-12 | *(chemical structure)* |
| I-13 | *(chemical structure)* |
| I-14 | *(chemical structure)* |

TABLE 1-continued
| Compound Number | Structure |
|---|---|
| I-15 | 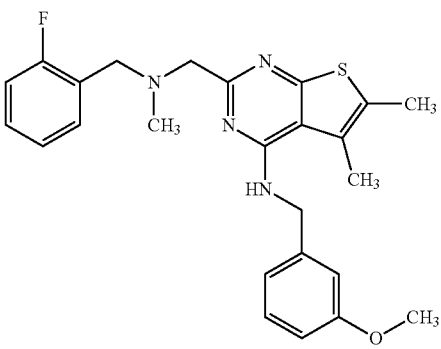 [SMILES: COc1cccc(CNc2nc(CN(C)Cc3ccccc3F)nc3sc(C)c(C)c23)c1] |
| I-16 | 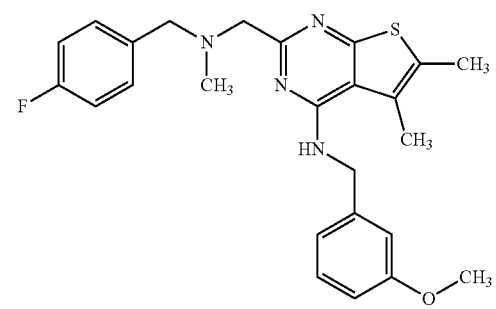 [SMILES: COc1cccc(CNc2nc(CN(C)Cc3ccc(F)cc3)nc3sc(C)c(C)c23)c1] |
| I-17 | 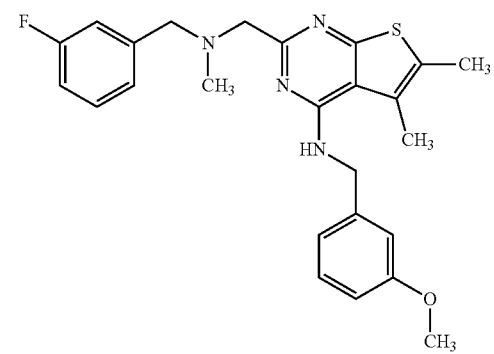 [SMILES: COc1cccc(CNc2nc(CN(C)Cc3cccc(F)c3)nc3sc(C)c(C)c23)c1] |
| I-18 | 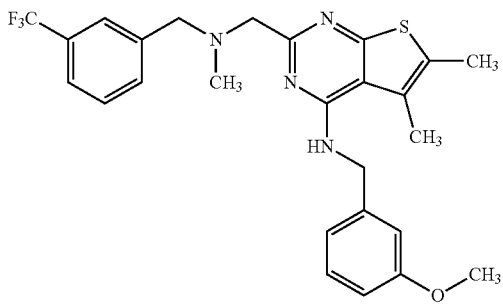 [SMILES: COc1cccc(CNc2nc(CN(C)Cc3cccc(C(F)(F)F)c3)nc3sc(C)c(C)c23)c1] |

TABLE 1-continued
| Compound Number | Structure |
| --- | --- |
| I-19 | 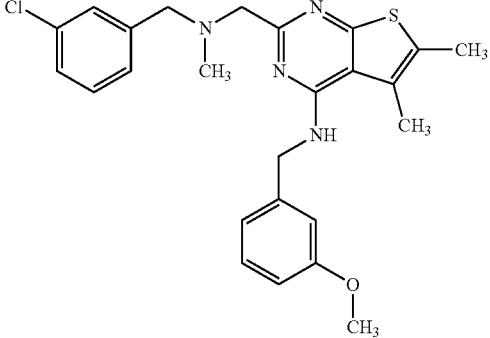 [SMILES: COc1cccc(CNc2nc(CN(C)Cc3cccc(Cl)c3)nc3sc(C)c(C)c23)c1] |
| I-20 | 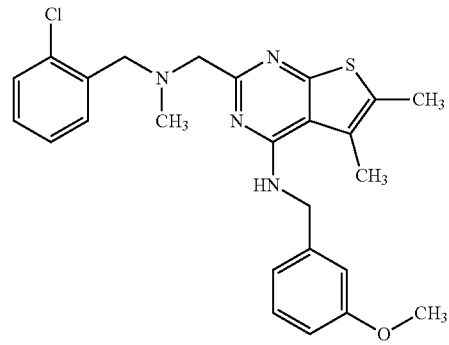 |
| I-21 | 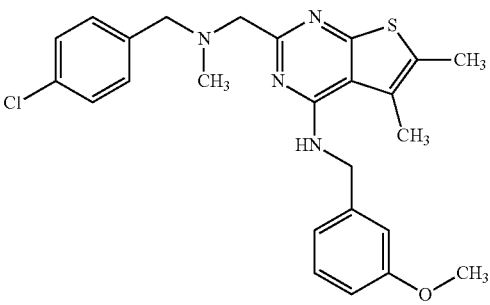 [SMILES: COc1cccc(CNc2nc(CN(C)Cc3ccc(Cl)cc3)nc3sc(C)c(C)c23)c1] |
| I-22 | 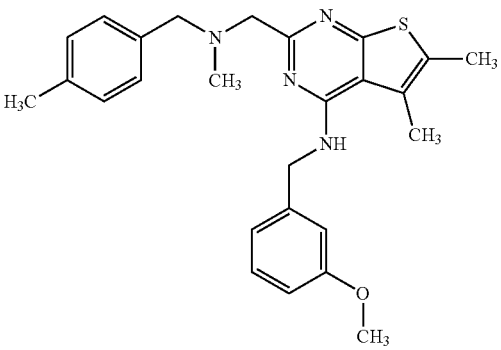 |

TABLE 1-continued

| Compound Number | Structure |
|---|---|
| I-23 | 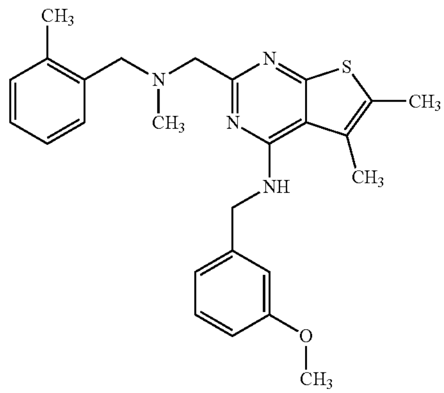 [SMILES: COc1cccc(CNc2nc(CN(C)Cc3ccccc3C)nc3sc(C)c(C)c23)c1] |
| I-24 | 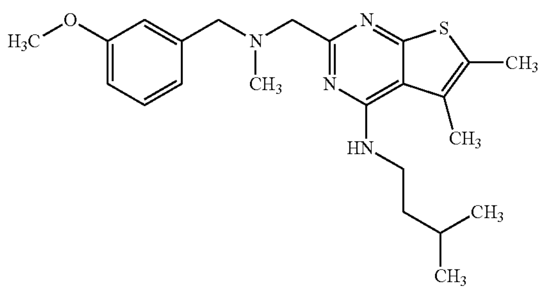 |
| I-25 | 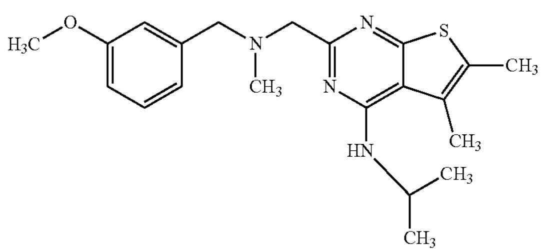 |
| I-26 | 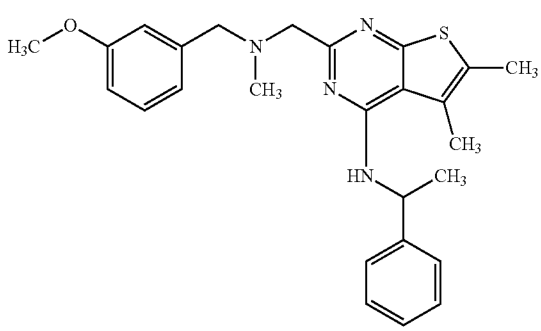 |
| I-27 | 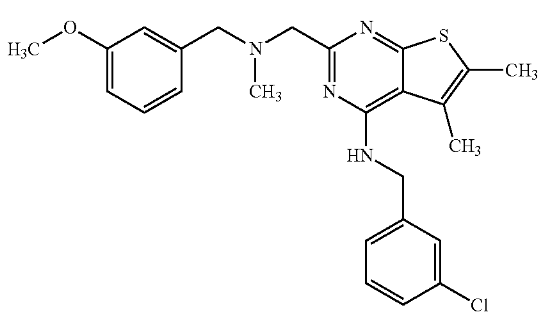 |

TABLE 1-continued

| Compound Number | Structure |
|---|---|
| I-28 | *(structure: 3-methoxybenzyl-N-methyl-aminomethyl-thieno[2,3-d]pyrimidine with 5,6-dimethyl and 4-(3-fluorobenzylamino) substituents)* |
| I-29 | *(structure: 3-methylbenzyl-N-methyl-aminomethyl-thieno[2,3-d]pyrimidine with 5,6-dimethyl and 4-(3-methoxybenzylamino) substituents)* |
| I-30 | *(structure: 3-methoxybenzyl-N-methyl-aminomethyl-thieno[2,3-d]pyrimidine with 5-methyl and 4-(3-methoxybenzylamino) substituents)* |
| I-31 | *(structure: 3-methoxybenzyl-N-methyl-aminomethyl-thieno[2,3-d]pyrimidine with 6-ethyl and 4-(3-methoxybenzylamino) substituents)* |
| I-32 | *(structure: 3-methoxybenzyl-N-methyl-aminomethyl-thieno[2,3-d]pyrimidine with 4-(3-methoxybenzylamino) substituent)* |

TABLE 1-continued

| Compound Number | Structure |
| --- | --- |
| I-33 | 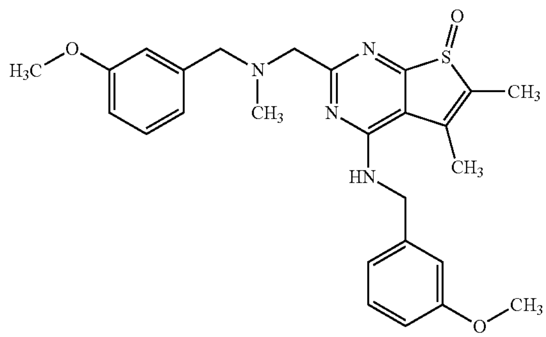 |
| I-34 | 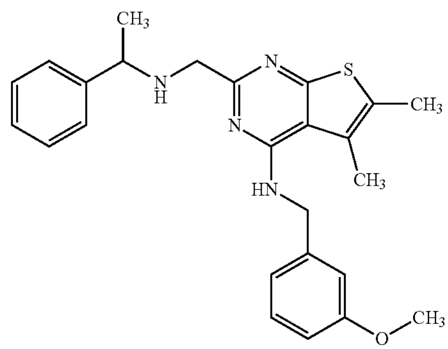 [SMILES: COc1cccc(CNc2nc(CNC(C)c3ccccc3)nc3sc(C)c(C)c23)c1] |
| I-35 | 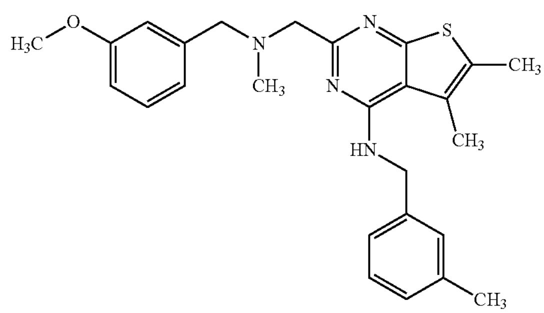 |
| I-36 | 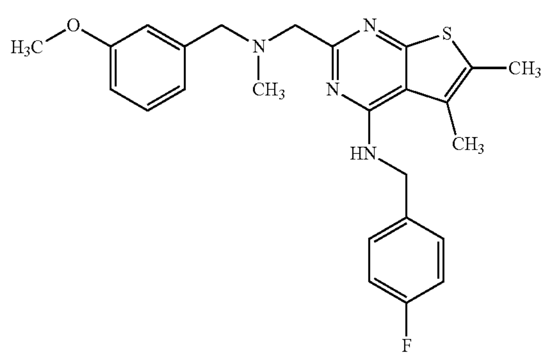 |

TABLE 1-continued

| Compound Number | Structure |
|---|---|
| I-37 | (3-methoxybenzyl)(methyl)aminomethyl-N-(2-fluorobenzyl)-5,6-dimethylthieno[2,3-d]pyrimidin-4-amine |
| I-38 | (3-methoxybenzyl)(methyl)aminomethyl-N-(3-(trifluoromethoxy)benzyl)-5,6-dimethylthieno[2,3-d]pyrimidin-4-amine |
| I-39 | (3-methoxybenzyl)(methyl)aminomethyl-N-(3-(trifluoromethyl)benzyl)-5,6-dimethylthieno[2,3-d]pyrimidin-4-amine |
| I-40 | (3-methoxybenzyl)(methyl)aminomethyl-N-(2-chlorobenzyl)-5,6-dimethylthieno[2,3-d]pyrimidin-4-amine |
| I-41 | (3-methoxybenzyl)(methyl)aminomethyl-N-(4-chlorobenzyl)-5,6-dimethylthieno[2,3-d]pyrimidin-4-amine |

TABLE 1-continued

| Compound Number | Structure |
|---|---|
| I-42 | 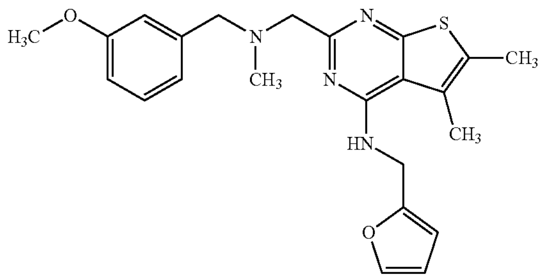 |
| I-43 | 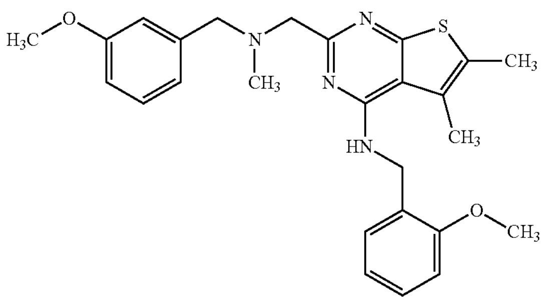 |
| I-44 | 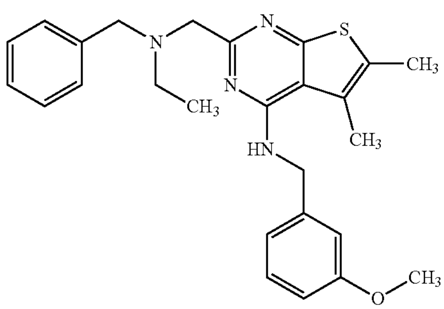 [SMILES: CCN(Cc1ccccc1)Cc1nc(NCc2cccc(OC)c2)c2c(C)c(C)sc2n1] |
| I-45 | 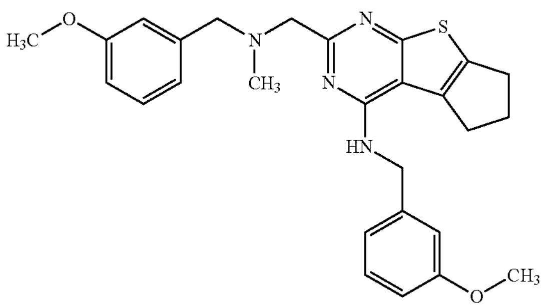 |
| I-46 | 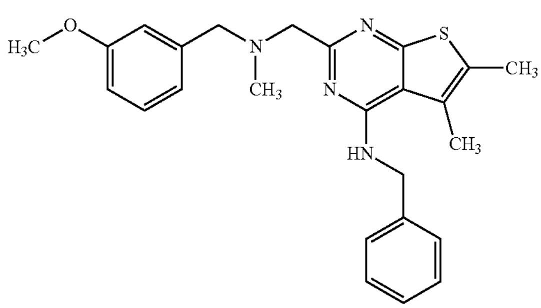 |

TABLE 1-continued

| Compound Number | Structure |
|---|---|
| I-47 | 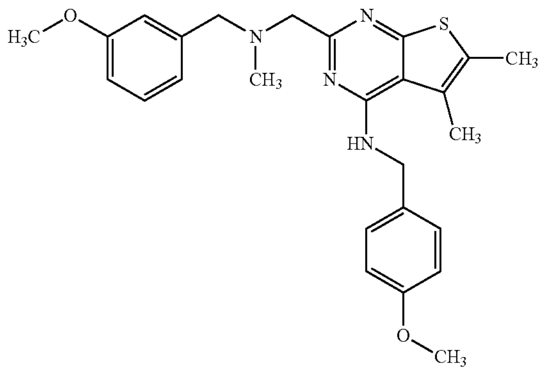 |
| I-48 | 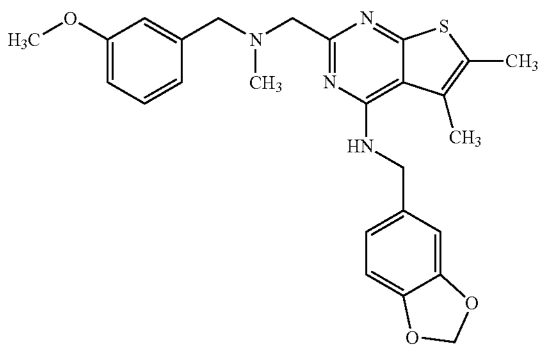 |
| I-49 | 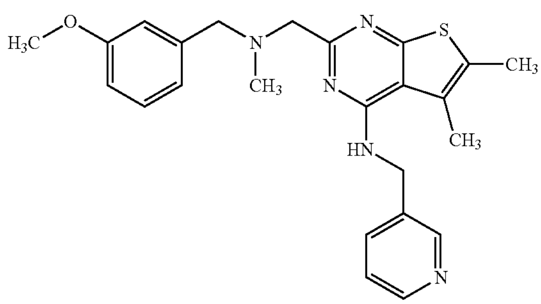 |
| I-50 | 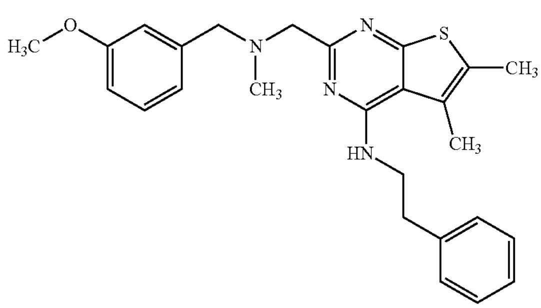 [SMILES: COc1cccc(CN(C)Cc2nc(NCCc3ccccc3)c3c(C)c(C)sc3n2)c1] |
| I-51 | 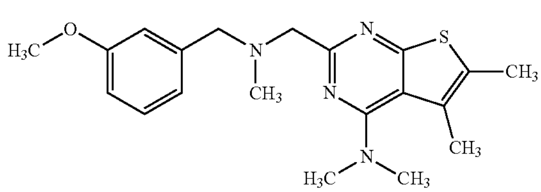 |

TABLE 1-continued

| Compound Number | Structure |
|---|---|
| I-52 | *(structure: 3-methoxybenzyl-N(CH3)-CH2-thienopyrimidine with 5,6-dimethyl and 4-NH-ethyl)* |
| I-53 | *(structure: 3-methoxybenzyl-N(CH3)-CH2-thienopyrimidine with 5,6-dimethyl and 4-N(CH3)-3-methoxybenzyl)* |
| I-54 | *(structure: benzyl-N(CH3)-CH2-thienopyrimidine with 5,6-dimethyl and 4-NH-3-methoxybenzyl)* |

In some embodiments, one or more of compounds I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, or I-54 are excluded from the compounds of the invention (e.g., Formula (I)). In certain embodiments, compound I-1 is excluded from the compounds of the invention (e.g., Formula (I)).

In some embodiments, the compounds of the invention include one or more of I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, or I-54. In some embodiments, the compounds of the invention include one or more of I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, or I-54. In some embodiments, the compounds of the invention include I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, and I-54. In some embodiments, the compounds of the invention include I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, and I-54.

In some embodiments, $R^1$ is not H, $R^2$ is not H, $R^3$ is not H, $R^4$ is not 3-methoxyphenyl, $R^5$ is not 3-methoxyphenyl, X is not

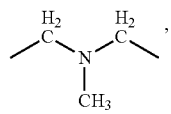

or ring A is not

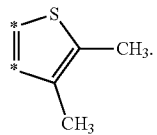

In other embodiments, one or more (e.g., one, two, three, or four) of the following provisos apply to Formula (I): $R^1$ is not H, $R^2$ is not H, $R^3$ is not H, $R^4$ is not 3-methoxyphenyl, $R^5$ is not 3-methoxyphenyl, X is not

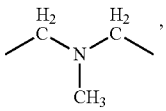

or ring A is not

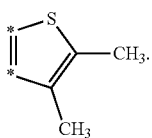

In some embodiments, $R^5$ is not 3-methoxyphenyl. In other embodiments, X is not

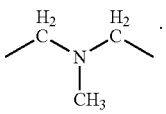

In some embodiments, the compounds of Formula (I) can be in the form of salts, optical and geometric isomers, and salts of isomers. In other embodiments, the compounds can be in various forms, such as uncharged molecules, components of molecular complexes, or non-irritating pharmacologically acceptable salts, including but not limited to hydrochloride, hydrobromide, sulphate, phosphate, nitrate, borate, acetate, maleate, tartrate, and salicylate. In some instances, for acidic compounds, salts can include metals, amines, or organic cations (e.g. quaternary ammonium). In yet other embodiments, simple derivatives of the compounds (e.g., ethers, esters, or amides) which have desirable retention and release characteristics but which are easily hydrolyzed by body pH, enzymes, or other suitable means, can be employed.

In some embodiments, the compounds of the invention having a chiral center and can exist in and be isolated in optically active and racemic forms. In other embodiments, compounds may exhibit polymorphism. Some embodiments of the present invention encompass any racemic, optically active, polymorphic, or stereoisomeric form, or mixtures thereof, of a compound described herein. The preparation of optically active forms can be accomplished by any suitable method, including but not limited to, resolution of the racemic form by recrystallization techniques, synthesis from optically-active starting materials, chiral synthesis, or chromatographic separation using a chiral stationary phase.

In some embodiments, the compounds of the invention (e.g., Formula (I), I-1, or I-2) can inhibit the activity of a member of the RalGEF family (e.g., RalGDS, RGL1, RGL2, RGL3) or a combination thereof. In certain embodiments, the compounds of the invention (e.g., Formula (I), I-1, or I-2) can inhibit the activity of RalGDS and RGL2. In other embodiments, the compounds of the invention (e.g., Formula (I), I-1, or I-2) can be a pan-RalGEF inhibitor. In other embodiments, the compounds of the invention (e.g., Formula (I), I-1, or I-2) can inhibit the interaction of K-Ras with RalGDS and can inhibit the interaction of K-Ras with RGL2. In still other embodiments, the compounds of the invention (e.g., Formula (I), I-1, or I-2) can promote cell cycle arrest/senescence, promote apoptosis, suppress Ral induced secretion, suppress the activation of the NFkB pathway in Ras driven pancreatic carcinoma cells, block the growth and development of cancer stem cells, suppress mitochondrial fission components, or a combination thereof.

In certain embodiments, one or more compounds of the invention (e.g., Formula (I)) can be part of a composition and can be in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, or no more than about 99.99%, from about 0.0001% to about 99%, from about 0.0001% to about 50%, from about 0.01% to about 95%, from about 1% to about 95%, from about 10% to about 90%, or from about 25% to about 75%.

In some embodiments, one or more compounds of the invention (e.g., Formula (I)) can be purified or isolated in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.0001% to about 99%, from about 0.0001% to about 50%, from about 0.01% to about 95%, from about 1% to about 95%, from about 10% to about 90%, or from about 25% to about 75%.

Some embodiments of the present invention include compositions comprising one or more compounds of the invention (e.g., Formula (I)). In certain embodiments, the composition is a pharmaceutical composition, such as compositions that are suitable for administration to animals (e.g., mammals, primates, monkeys, humans, canine, feline, porcine, mice, rabbits, or rats). In some instances, the pharmaceutical composition is non-toxic, does not cause side effects, or both. In some embodiments, there may be inherent side effects (e.g., it may harm the patient or may be toxic or harmful to some degree in some patients).

"Therapeutically effective amount" means an amount effective to achieve a desired and/or beneficial effect. An effective amount can be administered in one or more administrations. For some purposes of this invention, a therapeutically effective amount is an amount appropriate to treat an indication. By treating an indication is meant achieving any desirable effect, such as one or more of palliate, ameliorate, stabilize, reverse, slow, or delay disease progression, increase the quality of life, or to prolong life. Such achievement can be measured by any suitable method, such as measurement of tumor size.

In some embodiments, one or more compounds of the invention (e.g., Formula (I)) can be part of a pharmaceutical composition and can be in an amount of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.001% to about 99%, from about 0.001% to about 50%, from about 0.1% to about 99%, from about 1% to about 95%, from about 10% to about 90%, or from about 25% to about 75%. In some embodiments, the pharmaceutical composition can be presented in a dosage form which is suitable for the topical, subcutaneous, intrathecal, intraperitoneal, oral, parenteral, rectal, cutaneous, nasal, vaginal, or ocular administration route. In other embodiments, the pharmaceutical composition can be presented in a dosage form which is suitable for parenteral administration, a mucosal administration, intravenous administration, subcutaneous administration, topical administration, intradermal administration, oral administration, sublingual administration, intranasal administration, or intramuscular administration. The pharmaceutical composition can be in the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

In some embodiments, the pharmaceutical composition can include one or more formulary ingredients. A "formulary ingredient" can be any suitable ingredient (e.g., suitable for the drug(s), for the dosage of the drug(s), for the timing of release of the drugs(s), for the disease, for the disease state, or for the delivery route) including, but not limited to, water (e.g., boiled water, distilled water, filtered water, pyrogen-free water, or water with chloroform), sugar (e.g., sucrose, glucose, mannitol, sorbitol, xylitol, or syrups made therefrom), ethanol, glycerol, glycols (e.g., propylene glycol), acetone, ethers, DMSO, surfactants (e.g., anionic surfactants, cationic surfactants, zwitterionic surfactants, or nonionic surfactants (e.g., polysorbates)), oils (e.g., animal oils, plant oils (e.g., coconut oil or arachis oil), or mineral oils), oil derivatives (e.g., ethyl oleate, glyceryl monostearate, or hydrogenated glycerides), excipients, preservatives (e.g., cysteine, methionine, antioxidants (e.g., vitamins (e.g., A, E, or C), selenium, retinyl palmitate, sodium citrate, citric acid, chloroform, or parabens, (e.g., methyl paraben or propyl paraben)), or combinations thereof.

In certain embodiments, pharmaceutical compositions can be formulated to release the active ingredient (e.g., one or more compounds of the invention such as Formula (I)) substantially immediately upon the administration or any substantially predetermined time or time after administration. Such formulations can include, for example, controlled release formulations such as various controlled release compositions and coatings.

Other formulations (e.g., formulations of a pharmaceutical composition) can, in certain embodiments, include those incorporating the drug (or control release formulation) into food, food stuffs, feed, or drink.

Other embodiments of the invention can include methods of administering or treating an organism, which can involve treatment with an amount of at least one compound of the invention (e.g., Formula (I)) that is effective to treat the disease, condition, or disorder that the organism has, or is suspected of having, or is susceptible to, or to bring about a desired physiological effect. In some embodiments, the composition or pharmaceutical composition comprises at least one compound of the invention (e.g., Formula (I)) which can be administered to an animal (e.g., mammals, primates, monkeys, or humans) in an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some conditions, the dosage can be about 0.5 mg/kg human body weight or about 6.5 mg/kg human body weight. In some instances, some animals (e.g., mammals, mice, rabbits, feline, porcine, or canine) can be administered a dosage of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. Of course, those skilled in the art will appreciate that it is possible to employ many concentrations in the methods of the present invention, and using, in part, the guidance provided herein, will be able to adjust and test any number of concentrations in order to find one that achieves the desired result in a given circumstance. In other embodiments, the compounds of the invention (e.g., Formula (I)) can be administered in combination with one or more other therapeutic agents for a given disease, condition, or disorder.

In some embodiments, the compositions can include a unit dose of one or more compounds of the invention (e.g., Formula (I)) in combination with a pharmaceutically acceptable carrier and, in addition, can include other medicinal agents, pharmaceutical agents, carriers, adjuvants, diluents, and excipients. In certain embodiments, the carrier, vehicle or excipient can facilitate administration, delivery and/or improve preservation of the composition. In other embodiments, the one or more carriers, include but are not limited to, saline solutions such as normal saline, Ringer's solution, PBS (phosphate-buffered saline), and generally mixtures of various salts including potassium and phosphate salts with or without sugar additives such as glucose. Carriers can include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents. In other embodiments, the one or more excipients can include, but are not limited to water, saline, dextrose, glycerol, ethanol, or the like, and combinations thereof. Nontoxic auxiliary substances, such as wetting agents, buffers, or emulsifiers may also be added to the composition. Oral formulations can include such normally employed excipients as, for example, pharmaceutical grades of mannitol, lactose, starch, magnesium stearate, sodium saccharine, cellulose, and magnesium carbonate.

Administration Routes and Treatments of Disease

The compounds of the invention (e.g., Formula (I), I-1, or I-2) can be administered to animals by any number of suitable administration routes or formulations. The compounds of the invention (e.g., Formula (I), I-1, or I-2) can also be used to treat animals for a variety of diseases.

Animals include but are not limited to mammals, primates, monkeys (e.g., macaque, rhesus macaque, or pig tail macaque), humans, canine, feline, bovine, porcine, avian (e.g., chicken), mice, rabbits, and rats. As used herein, the term "subject" refers to both human and animal subjects.

The route of administration of the compounds of the invention (e.g., Formula (I), I-1, or I-2) can be of any suitable route. Administration routes can be, but are not limited to the oral route, the parenteral route, the cutaneous route, the nasal route, the rectal route, the vaginal route, and the ocular route. In other embodiments, administration routes can be parenteral administration, a mucosal administration, intravenous administration, subcutaneous administration, topical administration, intradermal administration, oral administration, sublingual administration, intranasal administration, or intramuscular administration. The choice of administration route can depend on the compound identity (e.g., the physical and chemical properties of the compound) as well as the age and weight of the animal, the particular disease (e.g., cancer), and the severity of the disease (e.g., stage or severity of cancer). Of course, combinations of administration routes can be administered, as desired.

Some embodiments of the invention include a method for providing a subject with a composition comprising one or more compounds of the invention (e.g., Formula (I), I-1, or I-2) described herein (e.g., a pharmaceutical composition) which comprises one or more administrations of one or more such compositions; the compositions may be the same or different if there is more than one administration.

Diseases that can be treated in an animal (e.g., mammals, porcine, canine, avian (e.g., chicken), bovine, feline, primates, rodents, monkeys, rabbits, mice, rats, and humans) using a compound of the invention (e.g., Formula (I), I-1, or 1-2) include, but are not limited to cancers.

In some embodiments, cancers that can be treated in an animal (e.g., mammals, porcine, canine, avian (e.g., chicken), bovine, feline, primates, rodents, monkeys, rabbits, mice, rats, and humans) using a compound of the invention (e.g., Formula (I), I-1, or I-2) include, but are not limited to cancers associated with a RAS mutation. In some embodiments, cancers that can be treated include, but are not limited to, pancreatic cancer (e.g., pancreatic ductal adenocarcinoma), lung cancer, liver cancer, colorectal cancer (e.g., colon cancer or rectal cancer), melanoma (e.g., cutaneous malignant melanoma, melanoma tumorigenesis), bladder cancer, prostate cancer, malignant nerve sheath tumors, multiple myeloma, breast cancer, squamous cell carcinoma (e.g., head and neck squamous cell carcinoma), lymphoma, leukemia, bone marrow cancer, non-Hodgkin lymphoma (e.g., diffuse large B-cell lymphoma), glioblastoma multiforme, endometrial cancer, kidney cancer, basal cell carcinoma, thyroid cancer, neuroblastoma, ovarian cancer, renal cell carcinoma, hepatocellular carcinoma, colon cancer, chronic lymphocytic leukemia (CLL), acute lymphoblastic leukemia, rhabdomyosarcoma, meningioma, gastric cancer, Glioma, oral cancer, nasopharyngeal carcinoma, rectal cancer, stomach cancer, uterine cancer, medulloblastoma, cancers that can result in metastasis, cancers resulting from metastasis, or cancerous tumors thereof. In some embodiments, cancers that can be treated include, but are not limited to, pancreatic cancer (e.g., pancreatic ductal adenocarcinoma), lung cancer, liver cancer, colorectal cancer (e.g., colon cancer or rectal cancer), melanoma (e.g., cutaneous malignant melanoma, melanoma tumorigenesis), bladder cancer, malignant nerve sheath tumors, multiple myeloma, breast cancer, squamous cell carcinoma (e.g., head and neck squamous cell carcinoma), ovarian cancer, prostate cancer, medulloblastoma, cancers that can result in metastasis (e.g., pancreatic cancer), cancers resulting from metastasis (e.g., lung cancer), or cancerous tumors thereof. In some embodiments, cancers that can be treated include, but are not limited to, pancreatic cancer (e.g., pancreatic ductal adenocarcinoma), lung cancer, liver cancer, ovarian cancer, prostate cancer, medulloblastoma, or cancerous tumors thereof. In some embodiments, cancers that can be treated include, but are not limited to, pancreatic cancer (e.g., pancreatic ductal adenocarcinoma) or cancerous tumors thereof. Animals that can be treated include but are not limited to mammals, rodents, primates, monkeys (e.g., macaque, rhesus macaque, pig tail macaque), humans, canine, feline, porcine, avian (e.g., chicken), bovine, mice, rabbits, and rats. As used herein, the term "subject" refers to both human and animal subjects. In some instances, the animal is in need of the treatment (e.g., by showing signs of disease or cancer, or by having a cancerous tumor).

In some embodiments, cancers that can be treated in an animal (e.g., mammals, porcine, canine, avian (e.g., chicken), bovine, feline, primates, rodents, monkeys, rabbits, mice, rats, and humans) using a compound of the invention (e.g., Formula (I), I-1, or I-2) include, but are not limited to cancers that can be treated by inhibiting (e.g., reducing the activity or expression of) a member of the RalGEF family (e.g., RalGDS or RGL2), by inhibiting RalGDS, by inhibiting RGL2, or combinations thereof. In some embodiments, cancers that can be treated in an animal include cancers that can be treated by inhibiting both RalGDS and RGL2.

As used herein, the term "treating" (and its variations, such as "treatment") is to be considered in its broadest context. In particular, the term "treating" does not necessarily imply that an animal is treated until total recovery. Accordingly, "treating" includes amelioration of the symptoms, relief from the symptoms or effects associated with a condition, decrease in severity of a condition, or preventing, preventively ameliorating symptoms, or otherwise reducing the risk of developing a particular condition. As used herein, reference to "treating" an animal includes but is not limited to prophylactic treatment and therapeutic treatment. Any of the compositions (e.g., pharmaceutical compositions) described herein can be used to treat an animal.

As related to treating cancer (e.g., pancreatic cancer (e.g., pancreatic ductal adenocarcinoma), lung cancer, liver cancer, colorectal cancer (e.g., colon cancer or rectal cancer), melanoma (e.g., cutaneous malignant melanoma, melanoma tumorigenesis), bladder cancer, ovarian cancer, prostate cancer, medulloblastoma, or cancerous tumors thereof), treating can include but is not limited to prophylactic treatment and therapeutic treatment. As such, treatment can include, but is not limited to: preventing cancer (e.g., pancreatic cancer (e.g., pancreatic ductal adenocarcinoma), lung cancer, liver cancer, colorectal cancer (e.g., colon cancer or rectal cancer), melanoma (e.g., cutaneous malignant melanoma, melanoma tumorigenesis), bladder cancer, ovarian cancer, prostate cancer, medulloblastoma, or cancerous tumors thereof); reducing the risk of cancer (e.g., pancreatic cancer (e.g., pancreatic ductal adenocarcinoma), lung cancer, liver cancer, colorectal cancer (e.g., colon cancer or rectal cancer), melanoma (e.g., cutaneous malignant melanoma, melanoma tumorigenesis), bladder cancer, ovarian cancer, prostate cancer, medulloblastoma, or cancerous tumors thereof); ameliorating or relieving symptoms of cancer (e.g., pancreatic cancer (e.g., pancreatic ductal adenocarcinoma), lung cancer, liver cancer, colorectal cancer (e.g., colon cancer or rectal cancer), melanoma (e.g., cutaneous malignant melanoma, melanoma tumorigenesis), bladder cancer, ovarian cancer, prostate cancer, medulloblastoma, or cancerous tumors thereof); eliciting a bodily response against cancer (e.g., pancreatic cancer (e.g., pancreatic ductal adenocarcinoma), lung cancer, liver cancer, colorectal cancer (e.g., colon cancer or rectal cancer), melanoma (e.g., cutaneous malignant melanoma, melanoma tumorigenesis), bladder cancer, ovarian cancer, prostate cancer, medulloblastoma, or cancerous tumors thereof); inhibiting the development or progression of cancer (e.g., pancreatic cancer (e.g., pancreatic ductal adenocarcinoma), lung cancer, liver cancer, colorectal cancer (e.g., colon cancer or rectal cancer), melanoma (e.g., cutaneous malignant melanoma, melanoma tumorigenesis), bladder cancer, ovarian cancer, prostate cancer, medulloblastoma, or cancerous tumors thereof); inhibiting or preventing the onset of symptoms associated with cancer (e.g., pancreatic cancer (e.g., pancreatic ductal adenocarcinoma), lung cancer, liver cancer, colorectal cancer (e.g., colon cancer or rectal cancer), melanoma (e.g., cutaneous malignant melanoma, melanoma tumorigenesis), bladder cancer, ovarian cancer, prostate cancer, medulloblastoma, or cancerous tumors thereof); reducing the severity of cancer (e.g., pancreatic cancer (e.g., pancreatic ductal adenocarcinoma), lung cancer, liver cancer, colorectal cancer (e.g., colon cancer or rectal cancer), melanoma (e.g., cutaneous malignant melanoma, melanoma tumorigenesis), bladder cancer, ovarian cancer, prostate cancer, medulloblastoma, or cancerous tumors thereof); causing a regression of cancer (e.g., pancreatic cancer (e.g., pancreatic ductal adenocarcinoma), lung cancer, liver cancer, colorectal cancer (e.g., colon cancer or rectal cancer), melanoma (e.g., cutaneous malignant melanoma, melanoma tumorigenesis), bladder cancer, ovarian cancer, prostate cancer, medulloblastoma, or cancerous tumors thereof) or one or more of the symptoms associated with cancer (e.g., a decrease in tumor size); causing remission of cancer (e.g., pancreatic cancer (e.g., pancreatic ductal adenocarcinoma), lung cancer, liver cancer, colorectal cancer (e.g., colon cancer or rectal cancer), melanoma (e.g., cutaneous malignant melanoma, melanoma tumorigenesis), bladder cancer, ovarian cancer, prostate cancer, medulloblastoma, or cancerous tumors thereof); or preventing relapse of cancer (e.g., pancreatic cancer (e.g., pancreatic ductal adenocarcinoma), lung cancer, liver cancer, colorectal cancer (e.g., colon cancer or rectal cancer), melanoma (e.g., cutaneous malignant melanoma, melanoma tumorigenesis), bladder cancer, ovarian cancer, prostate cancer, medulloblastoma, or cancerous tumors thereof). In some embodiments, treating does not include prophylactic treatment of cancer (e.g., preventing or ameliorating future cancer).

Treatment of an animal can occur using any suitable administration method (such as those disclosed herein) and using any suitable amount of a compound of the invention (e.g., Formula (I), I-1, or I-2). In some embodiments, methods of treatment comprise treating an animal for cancer (e.g., pancreatic cancer (e.g., pancreatic ductal adenocarcinoma), lung cancer, liver cancer, colorectal cancer (e.g., colon cancer or rectal cancer), melanoma (e.g., cutaneous malignant melanoma, melanoma tumorigenesis), bladder cancer, ovarian cancer, prostate cancer, medulloblastoma, or cancerous tumors thereof). Some embodiments of the invention include a method for treating a subject (e.g., an animal such as a human or primate) with a composition comprising a compound of the invention (e.g., Formula (I), I-1, or I-2) (e.g., a pharmaceutical composition) which comprises one or more administrations of one or more such compositions; the compositions may be the same or different if there is more than one administration.

In some embodiments, the method of treatment includes administering an effective amount of a composition comprising a compound of the invention (e.g., Formula (I), I-1, or I-2). As used herein, the term "effective amount" refers to a dosage or a series of dosages sufficient to affect treatment (e.g., to treat cancer, such as but not limited to pancreatic cancer (e.g., pancreatic ductal adenocarcinoma), lung cancer, liver cancer, colorectal cancer (e.g., colon cancer or rectal cancer), melanoma (e.g., cutaneous malignant melanoma, melanoma tumorigenesis), bladder cancer, ovarian cancer, prostate cancer, medulloblastoma, or cancerous tumors thereof) in an animal. In some embodiments, an effective amount can encompass a therapeutically effective amount, as disclosed herein. In certain embodiments, an effective amount can vary depending on the subject and the particular treatment being affected. The exact amount that is required can, for example, vary from subject to subject, depending on the age and general condition of the subject, the particular adjuvant being used (if applicable), administration protocol, and the like. As such, the effective amount can, for example, vary based on the particular circumstances, and an appropriate effective amount can be determined in a particular case. An effective amount can, for example, include any dosage or composition amount disclosed herein. In some embodiments, an effective amount of at least one compound of the invention (e.g., Formula (I) such as but not limited to compounds I-1 or I-2) (which can be administered to an animal such as mammals, primates, monkeys or humans) can be an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some embodiments, the dosage can be about 0.5 mg/kg human body weight or about 6.5 mg/kg human body weight. In some instances, an effective amount of at least one compound of the invention (e.g., Formula (I) such as but not limited to compounds I-1 or I-2) (which can be administered to an animal such as mammals, rodents, mice, rabbits, feline, porcine, or canine) can be an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. In some embodiments, an effective amount of at least one compound of the invention (e.g., Formula (I) such as but not limited to compounds I-1 or I-2) (which can be administered to an animal such as mammals, primates, monkeys or humans) can be an amount of about 1 to about 1000 mg/kg body weight, about 5 to about 500 mg/kg body weight, about 10 to about 200 mg/kg body weight, about 25 to about 100 mg/kg body weight, about 1 mg/kg, about 2 mg/kg, about 5 mg/kg, about 10 mg/kg, about 25 mg/kg, about 50 mg/kg, about 100 mg/kg, about 150 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg. In regard to some conditions, the dosage can be about 20 mg/kg human body weight or about 100 mg/kg human body weight. In some instances, an effective amount of at least one compound of the invention (e.g., Formula (I) such as but not limited to compounds I-1 or I-2) (which can be administered to an animal such as mammals, rodents, mice, rabbits, feline, porcine, or canine) can be an amount of about 1 to about 1000 mg/kg body weight, about 5 to about 500 mg/kg body weight, about 10 to about 200 mg/kg body weight, about 25 to about 100 mg/kg body weight, about 1 mg/kg, about 2 mg/kg, about 5 mg/kg, about 10 mg/kg, about 25 mg/kg, about 50 mg/kg, about 100 mg/kg, about 150 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg.

"Therapeutically effective amount" means an amount effective to achieve a desired and/or beneficial effect (e.g., decreasing tumor size). A therapeutically effective amount can be administered in one or more administrations. For some purposes of this invention, a therapeutically effective amount is an amount appropriate to treat an indication (e.g., to treat cancer). By treating an indication is meant achieving any desirable effect, such as one or more of palliate, ameliorate, stabilize, reverse, slow, or delay disease (e.g., cancer) progression, increase the quality of life, or to prolong life. Such achievement can be measured by any suitable method, such as but not limited to measurement of tumor size.

In some embodiments, the treatments can also include one or more of surgical intervention, chemotherapy, radiation therapy, hormone therapies, immunotherapy, and adjuvant systematic therapies. Adjuvants may include but are not limited to chemotherapy (e.g., temozolomide), radiation therapy, antiangiogenic therapy (e.g., bevacizumab), and hormone therapies, such as administration of LHRH agonists; antiestrogens, such as tamoxifen; high-dose progestogens; aromatase inhibitors; and/or adrenalectomy. Chemotherapy can be used as a single-agent or as a combination with known or new therapies.

In some embodiments, the administration of at least one compound of the invention (e.g., Formula (I), I-1, or I-2) is an adjuvant cancer therapy or part of an adjuvant cancer therapy. Adjuvant treatments include treatments by the mechanisms disclosed herein and of cancers as disclosed herein, including, but not limited to tumors. Corresponding primary therapies can include, but are not limited to, surgery, chemotherapy, or radiation therapy. In some instances, the adjuvant treatment can be a combination of chemokine receptor antagonists with traditional chemotoxic agents or with immunotherapy that increases the specificity of treatment to the cancer and potentially limits additional systemic side effects. In still other embodiments, a compound of the invention (e.g., Formula (I), I-1, or I-2) can be used as adjuvant with other chemotherapeutic agents. The use of a compound of the invention (e.g., Formula (I), I-1, or I-2) may, in some instances, reduce the duration of the dose of both drugs and drug combinations reducing the side effects.

In some embodiments, the treatments disclosed herein can include use of other drugs (e.g., antibiotics) or therapies for treating disease. For example, antibiotics can be used to treat infections and can be combined with a compound of the invention to treat disease (e.g., infections associated with cancer). In other embodiments, intravenous immunoglobulin (IVIG) therapy can be used as part of the treatment regime (i.e., in addition to administration of the compound(s) of the invention).

Methods for Preparing Compounds of Formula (I)

Some embodiments of the present invention include methods for the preparation of compounds of Formula (I).

The compounds of Formula (I) can be prepared using any suitable method or they can be purchased, if available. In certain embodiments, a compound of Formula (I) can be prepared comprising the step of reacting a compound of Formula (II) with a compound of Formula (III) to result in Formula (IV), which is later made into Formula (I) (e.g., using one or more synthetic steps).

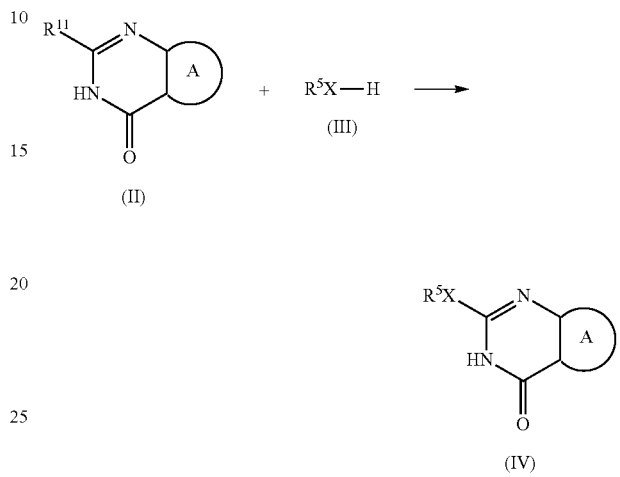

In some embodiments $R^{11}$ can be halogen (e.g., F, Cl, Br, or I) or —$CH_2$-halogen. In other embodiments, $R^{11}$ can be Cl or —$CH_2$Cl. In still other embodiments, $R^{11}$ can be —$CH_2$-halogen, —$CH_2$Br, or —$CH_2$Cl. $R^5$, X, and ring A of Formulas (II), (III), and (IV) are the same as that defined in Formula (I). Formula (II) can be prepared using any suitable method or can be purchased if available. Formula (III) can be prepared using any suitable method or can be purchased where available.

In some embodiments, Formula (II) can be reacted with Formula (III) under the following conditions: Formula (II) and Formula (III) can be in a mixture comprising a solvent (e.g., DMF). The mixture can be heated (e.g., using a microwave) at a certain temperature (e.g., about 120° C.) for a certain amount of time (e.g., about 2 hours). Formula (IV) can then optionally be recovered.

In some embodiments, Formula (III) (e.g., about 1.3 mL or about 1.34 g or about 8.86 mmol) is added to Formula (II) (e.g., about 718 mg or about 3.69 mmol) in about 6 mL (e.g., from about 1 mL to about 20 mL) of DMF (or any suitable solvent). The resulting solution is stirred at about 120° C. (or from about 90° C. to about 150° C.) for about 2 hours (or from about 0.5 hours to about 10 hours) under heat (e.g., microwave irradiation). After cooling to room temperature, the mixture can be poured into about 100 mL (or from about 20 mL to about 500 ml) of water. The aqueous mixture can stand for about 5 minutes (or from about 1 minute to about 25 minutes) and then be extracted three times (or from one time to 10 times) with about 75 mL portions (or from about 10 mL to about 500 mL) of ethyl acetate (or any suitable solvent). The combined organic layers can then be washed (e.g., with brine), dried (e.g., with $Na_2SO_4$) and concentrated (e.g., in vacuo). The crude product can be dissolved in minimal amount of ethyl acetate (or any suitable solvent) and can then be precipitated (e.g., by adding drops of hexanes (or any suitable solvent)) to provide Formula (IV).

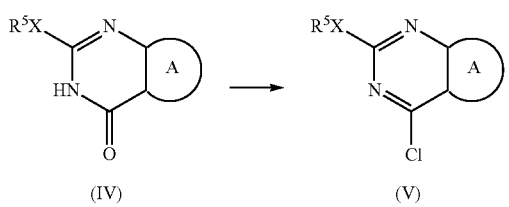

$R^5$, X, and ring A of Formula (IV) and Formula (V) are the same as that defined in Formula (I). Formula (IV) can be prepared using any suitable method (e.g., see above) or can be purchased if available.

In some embodiments, Formula (IV) can be reacted to provide Formula (V) under the following conditions: Formula (IV) can be mixed with POCl₃ (or any suitable compound to convert the oxo of Formula (IV) to Cl or other halogen) and is heated (e.g., with a microwave) at a certain temperature (e.g., about 90° C.) for a certain amount of time (e.g., about 3 hours). Formula (V) can then optionally be recovered.

Formula (IV) (e.g., about 309 mg or about 0.971 mmol) in about 3 mL (or from about 0.5 mL to about 20 mL) of POCl₃ (or any suitable compound to convert the oxo of Formula (IV) to Cl or other halogen, such as POBr₃) can be stirred at about 90° C. (or from about 30° C. to about 150° C.) for about 3 hours (or from about 0.5 hours to about 20 hours) under heat (e.g., microwave irradiation). After cooling (e.g., to room temperature), the solvent can be removed (e.g., under reduced pressure). The residue can be diluted with about 10 mL (or from about 2 mL to about 50 mL) of water (e.g., cold water) containing about 2 g (or from about 0.5 g to about 10 g) of a suitable salt (e.g., potassium carbonate). After sitting for about 5 minutes (or from about 0.5 minutes to about 50 minutes), the aqueous solution can be extracted twice (or once or up to 10 times) with about 10 mL (or from about 1 mL to about 100 mL) portions of any suitable solvent (e.g., ethyl acetate). The combined organic layers can be dried (e.g., using Na₂SO₄) and can be concentrated (e.g., in vacuo). The concentrate can then be chromatographed (e.g., over silica gel (Combiflash, 4 g column, 0-70%, hexanes-ethyl acetate, 10 minutes)) to provide Formula (V).

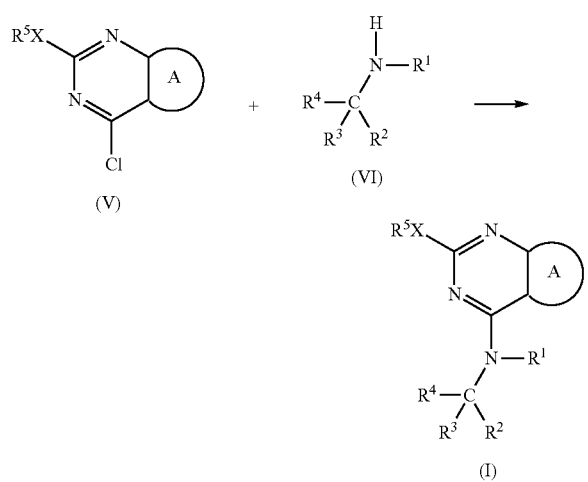

$R^1$, $R^2$, $R^3$, $R^4$, $R^5$, X and ring A of Formula (V) and Formula (VI) are the same as that defined in Formula (I).

Formula (V) can be prepared using any suitable method (e.g., see above) or can be purchased where available. Formula (VI) can be prepared using any suitable method or can be purchased if available.

In some embodiments, Formula (V) can be reacted with Formula (VI) to provide Formula (I) under the following conditions: Formula (V) and Formula (VI) can be in a mixture and heated (e.g., using a microwave) at a certain temperature (e.g., about 100° C.) for a certain amount of time (e.g., about 15 hours). Formula (I) can then optionally be recovered.

Formula (V) (e.g., about 208 mg or about 0.636 mmol) in about 20 mL (or from about 1 mL to about 200 mL) of tetrahydrofuran (or any suitable solvent) can be added to Formula (VI) (e.g., about 0.11 mL or about 113 mg or about 0.827 mmol) and to trimethylamine (or any suitable solvent) (e.g., about 0.44 mL or about 321 mg or about 3.18 mmol). The resulting solution can be stirred at about 100° C. (or from about 40° C. to about 300° C.) for about 15 hours (or about 2 hours to about 100 hours) under heat (e.g., microwave irradiation) and then can be cooled (e.g., to room temperature). The mixture can then be diluted with about 20 mL (or from about 2 mL to about 200 mL) of any suitable solvent (e.g., ethyl acetate) and then can be washed with water (e.g., washed 1, 2, 3, 4, or 5 times). The organic phase can be dried (e.g., using Na₂SO₄) and concentrated (e.g., in vacuo). The residue can then be chromatographed (e.g., over silica gel (Combiflash, 4 g column, 0-100%, hexanes-ethyl acetate, 11 minutes)) to provide Formula (I).

In some embodiments, Formula (I) (or any other formula recited above) can be recovered. Recovery can occur using any suitable method including but not limited to HPLC (e.g., reverse phase), LC, precipitation, centrifugation, column chromatography (e.g., size exclusion chromatography or ion exchange chromatography), use of silica gel, or combinations thereof.

In some embodiments, a method for the preparation of a compound of Formula (I) can comprise one or more of the above-mentioned steps. In certain embodiments, a method for preparing a compound of Formula (I) comprises
(a) reacting a compound of Formula (II) with a compound of Formula (III) to result in a mixture comprising a compound of Formula (IV);
(b) reacting a compound of Formula (IV) with a suitable compound (e.g., POCl₃ or POBr₃) to convert an oxo to a halogen (e.g., F, Cl, Br, or I) to result in a mixture comprising a compound of Formula (V);
(c) reacting a compound of Formula (V) with a compound of Formula (VI); and;
(d) recovering Formula (I).

The presently-disclosed subject matter is further illustrated by the following specific but non-limiting examples. The following examples may include compilations of data that are representative of data gathered at various times during the course of development and experimentation related to the present invention.

EXAMPLES

Example Set A

Synthetic Methods and Compound Characterization

Compound I-1 was purchased from Molplex (Newcastle upon Tyne, UK).

Compound I-2 is synthesized according to the following synthetic scheme, which is one example of how molecules of Formula (I) can be synthesized.

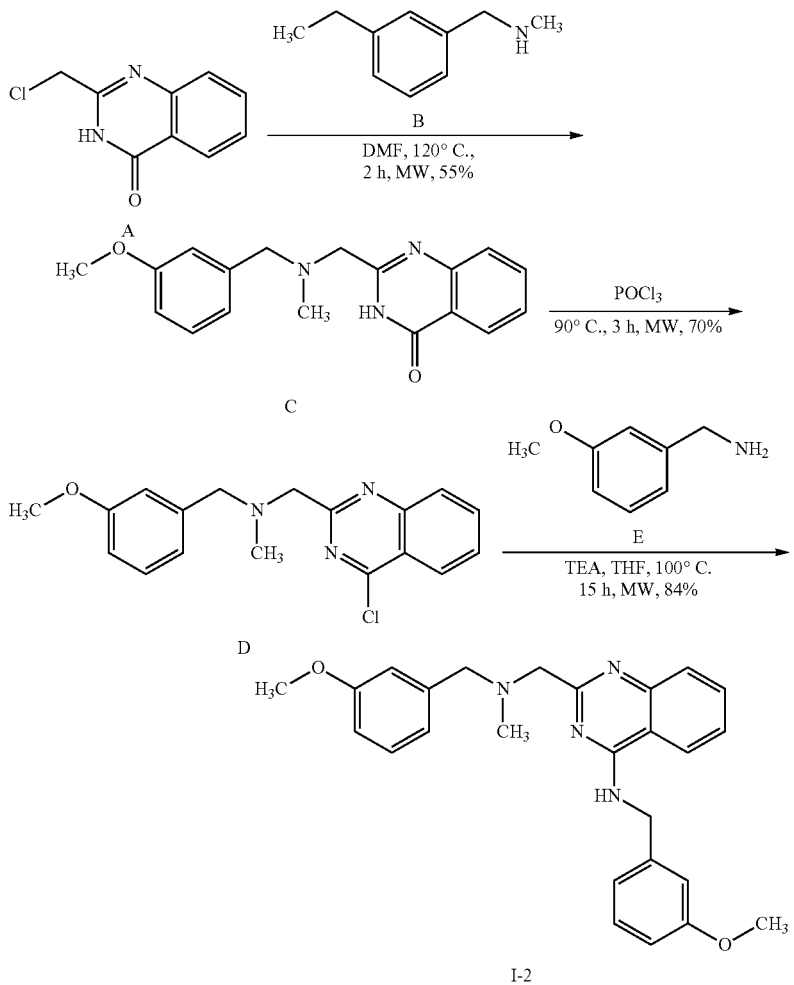

The synthesis began by reacting commercially available 2-(chloromethyl)-4(3H)-quinazolinone (A) with secondary amine B. The resulting quinazolinone C was treated with phosphoryl chloride, which furnished chloroquinazoline D. Subsequent aromatic substitution with 3-methoxybenzylamine (E) afforded compound I-2.

Synthesis of 2-(((3-Methoxybenzyl)(methyl)amino) methyl)quinazolin-4(3H)-one (C). To a solution of 718 mg (3.69 mmol) of 2-(chloromethyl)-4(3H)-quinazolinone (A) in 6 mL of DMF was added 1.3 mL (1.34 g, 8.86 mmol) of 1-(3-methoxyphenyl)-N-methylmethanamine (B). The resulting solution was stirred at 120° C. for 2 hours under microwave irradiation. After cooling to room temperature, the mixture was poured into 100 mL of water. The aqueous mixture stood for 5 minutes and then was extracted three times with 75-mL portions of ethyl acetate. The combined organic layers were washed with brine, dried (Na$_2$SO$_4$) and concentrated in vacuo. The crude product was dissolved in minimal amount of ethyl acetate and precipitated by adding drops of hexanes to afford 629 mg (55%) of C as a light orange solid: $^1$H NMR (400 MHz, DMSO-d$_6$) δ 11.95 (s, 1H), 8.12 (d, J=8.0 Hz, 1H), 7.80 (td, J=7.4, 1.2 Hz, 1H), 7.65 (d, J=8.4 Hz, 1H), 7.50 (t, J=7.6 Hz, 1H), 7.23 (t, J=8.0 Hz, 1H), 7.01 (s, 1H), 6.95 (d, J=7.6 Hz, 1H), 6.81 (dd, J=8.0, 2.4 Hz, 1H), 3.75 (s, 3H), 3.61 (s, 2H), 3.56 (s, 2H), 2.19 (s, 3H); $^{13}$C NMR (100.5 MHz, DMSO-d$_6$) δ 161.6, 159.2, 154.7, 148.4, 139.9, 134.3, 129.1, 127.0, 126.4, 125.8, 121.3, 121.1, 114.5, 112.5, 60.8, 59.8, 54.9, 41.5; ESI-HRMS m/z: [M+H]$^+$ calcd for C$_{18}$H$_{19}$N$_3$O$_2$ 310.1550, found 310.1462.

Synthesis of 1-(4-Chloroquinazolin-2-yl)-N-(3-methoxybenzyl)-N-methylmethanamine (D). A solution of 309 mg (0.971 mmol) of quinazolinone C in 3 mL of POCl$_3$ was stirred at 90° C. for 3 hours under microwave irradiation. After cooling to room temperature, the solvent was carefully removed under reduced pressure. The residue was slowly diluted with 10 mL of cold water containing 2 g of potassium carbonate. After sitting for 5 minutes, the aqueous solution was extracted twice with 10-mL portions of ethyl acetate. The combined organic layers were dried (Na$_2$SO$_4$) and concentrated in vacuo. The crude product was chromatographed over silica gel (Combiflash, 4 g column, 0-70%, hexanes-ethyl acetate, 10 minutes) to afford 222 mg (70%) of D as a yellow oil: $^1$H NMR (400 MHz, CDCl$_3$) δ 8.25 (dd, J=8.4, 0.8 Hz, 1H), 8.09 (d, J=8.0 Hz, 1H), 7.94 (dd, J=7.2, 1.6 Hz, 1H), 7.69 (dd, J=7.2, 1.2 Hz, 1H), 7.21 (t, J=8.0 Hz, 1H), 7.04 (s, 1H), 6.98 (d, J=7.6 Hz, 1H), 6.78 (dd, J=7.8, 2.2 Hz, 1H), 3.99 (s, 2H), 3.82 (s, 3H), 3.73 (s, 2H), 2.44 (s, 3H); $^{13}$C NMR (100.5 MHz, CDCl$_3$) δ 163.6, 162.5, 159.6, 151.3, 140.0, 134.8, 129.1, 128.6, 128.4, 125.7, 122.4, 121.6, 114.3, 113.0, 63.2, 61.8, 55.2, 42.9; ESI-HRMS m/z: [M+H]$^+$ calcd for $C_{18}H_{18}ClN_3O$ 328.1211, found 328.1203.

Synthesis of N-(3-Methoxybenzyl)-2-(((3-methoxybenzyl)(methyl)amino)methyl)quinazolin-4-amine (Compound I-2). To a solution of 208 mg (0.636 mmol) of chloroquinazoline D in 20 mL of tetrahydrofuran was added 0.11 mL (113 mg, 0.827 mmol) of 3-methoxybenzylamine (E) and 0.44 mL (321 mg, 3.18 mmol) of trimethylamine. The resulting solution was stirred at 100° C. for 15 hours under microwave irradiation and then was cooled to room temperature. The mixture was diluted with 20 mL of ethyl acetate and then washed with water. The organic phase was dried ($Na_2SO_4$) and concentrated in vacuo. The residue was chromatographed over silica gel (Combiflash, 4 g column, 0-100%, hexanes-ethyl acetate, 11 minutes) to afford 230 mg (84%) of compound I-2 as an orange oil: $^1$H NMR (400 MHz, CDCl$_3$) δ 7.89 (d, J=8.4 Hz, 1H), 7.71 (dd, J=8.4, 1.2 Hz, 1H), 7.67 (d, J=8.0 Hz, 1H), 7.41 (dd, J=7.6, 1.2 Hz, 1H), 7.29 (t, J=8.0 Hz, 1H), 7.19 (t, J=8.0 Hz, 1H), 7.04 (s, 1H), 7.00 (s, 1H), 6.99 (s, 1H), 6.96 (s, 1H), 6.84 (dd, J=8.4, 2.8 Hz, 1H), 6.77 (dd, J=8.4, 2.8 Hz, 1H), 5.90 (s, 1H), 4.89 (d, J=5.6 Hz, 2H), 3.84 (s, 2H), 3.77 (s, 6H), 3.74 (s, 2H), 2.41 (s, 3H); $^{13}$C NMR (100.5 MHz, CDCl$_3$) δ 164.2, 159.9, 159.5, 159.3, 150.1, 140.9, 140.1, 132.4, 129.8, 128.9, 128.6, 125.5, 121.6, 120.3 (2C), 114.4, 113.8, 113.4, 112.9, 112.6, 64.1, 61.7, 55.2 (2C), 45.3, 42.7; ESI-HRMS m/z: [M+H]$^+$ calcd for $C_{26}H_{28}N_4O_2$ 429.2285, found 429.2286.

Example Set B

Biological Characterization

Inhibition of Soft Agar Growth:

FIG. 1. Effects of some compounds of Formula (I) on RalGEF inhibitor on soft agar growth and normal growth in 2D of pancreatic carcinoma cell lines. In FIGS. 1A and 1B, Panc-1 (ATCC® CRL-1469™) and MiaPaCa-2 (ATCC® CRL-1420™) mutant Ras containing pancreatic tumor cell lines were plated in soft agar in the presence of 10 μM or 0.9 μM of compound I-1 and scored for the formation of colonies. In FIGS. 1C and 1D, compound I-1 was then tested for the ability to inhibit cell growth on the same cell lines under normal 2D growth conditions on plastic. "0" is the carrier. Cells were seeded at the same density and scored after two weeks in culture.

Figure 1B:
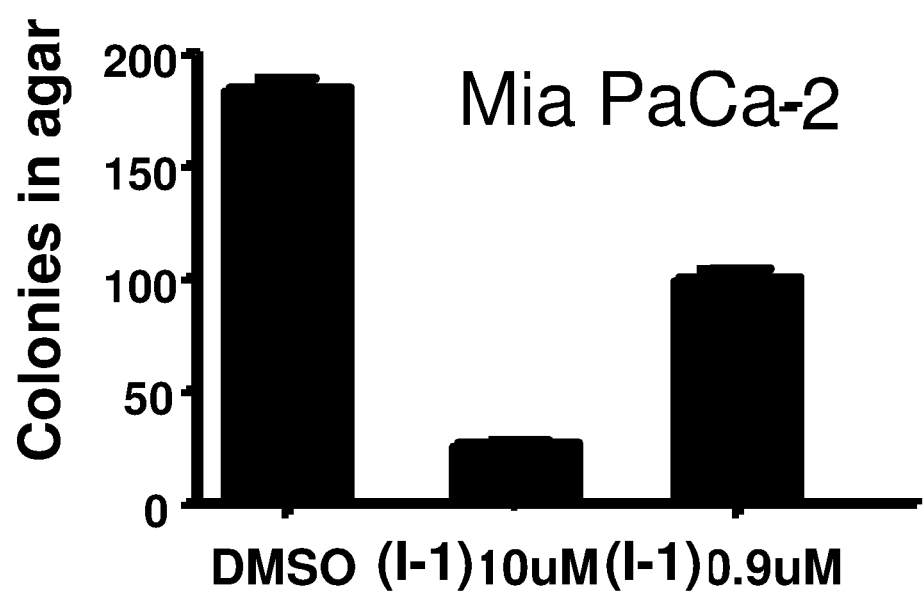

Compound I-1 blocks the tumorigenic phenotype in vitro at low μM or sub μM levels for Panc1 and Mia PaCa-2 (FIGS. 1A and 1B). Compound I-1 also blocks the tumorigenic phenotype in vitro (data not shown) of the following Ras driven tumor cell lines Caov-3 [Caov3] (ATCC® HTB-75™)(ovarian cancer); D283 Med (ATCC® HTB-185™) (Medulloblastoma); A549 (ATCC® CCL-185™) (lung cancer); and LNCaP clone FGC (ATCC® CRL1740™) (prostate cancer).

Human pancreatic tumor cell lines MiaPaca-2 and Panc-1 contain activated K-Ras and were used in the initial screen to identify compound I-1. Soft agar colony formation remains an established in vitro assay to predict tumorigenicity and was used to predict tumorigenicity for compound I-1. Quantitative assays showed that 10 μM of compound I-1 almost completely blocked the ability of the cells to grow in soft agar (FIGS. 1A and 1B). Titration experiments showed that compound I-1 exhibited an IC50 (i.e., a concentration that inhibits 50% of colony formation) of less than ~1 μM (data not shown).

Several other compounds were tested against the Mia Paca-2 cell line using the soft agar colony formation in vitro assay in two experiments. The results for the two experiments are shown in Tables 2 and 3. For each table, DMSO was used as a control and, as such, within each table, the DMSO colonies are the measure against which each measurement in the corresponding table is compared.

TABLE 2

| Compound (all concentrations 10 μM) | Colonies in agar |
| --- | --- |
| DMSO | 182 ± 7 |
| I-1 | 0 ± 0 |
| I-26 | 0 ± 0 |
| I-27 | 51 ± 9 |
| I-28 | 54 ± 5 |
| I-29 | 0 ± 0 |
| I-30 | 14 ± 2 |
| I-31 | 14 ± 1 |
| I-32 | 36 ± 1 |
| I-33 | 186 ± 4 |

TABLE 3

| Compound (concentration in μM) | Colonies in agar |
| --- | --- |
| DMSO | 1686 ± 114 |
| I-45 (10 μM) | 361 ± 49 |
| I-54 (10 μM) | 410 ± 31 |
| I-43 (10 μM) | 272 ± 40 |
| I-46 (10 μM) | 320 ± 22 |
| I-1 (10 μM) | 12 ± 1 |

Without being limited by theory, one of the advantages of RalGEFs as targets is that their activation can result in transformation, but their activation does not impact normal growth (e.g., in a plate-attached 2D culture). Therefore, according to this theory, a RalGEF inhibitor should block agar growth, but have little effect on normal 2D growth.

Figure 1C:
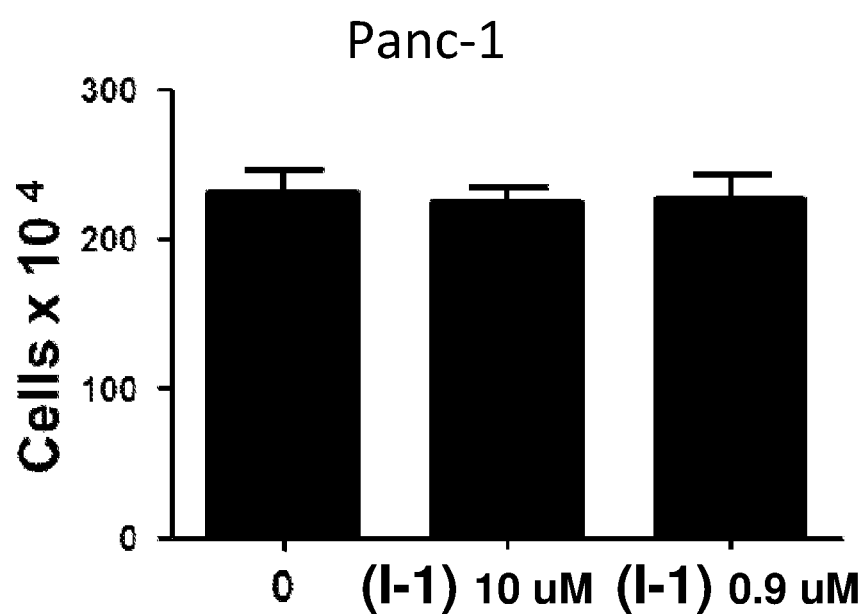
FIGS. 1C and 1D: Compound I-1 was tested for the ability to inhibit cell growth on the same cell lines (Panc-1 (FIG. 1C) and MiaPaCa-2 (FIG. 1D)) under normal 2D growth conditions on plastic. 0=carrier. Cells were seeded at the same density and scored after one week in culture.
Figure 1D:
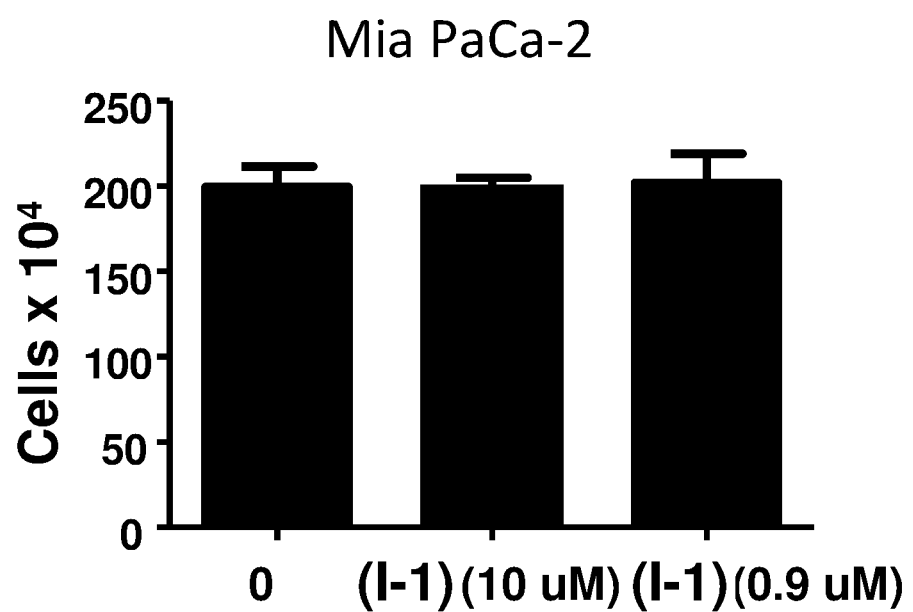

When we assayed compound I-1 against the same cell lines grown in 2D, we could detect no reduction in growth over the course of 1 week (FIGS. 1C and 1D). Compound I-2, has a similar effect to compound I-1 (data not shown).

Figure 2A:
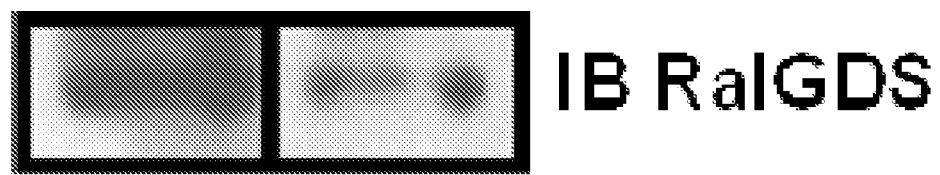
FIG. 2A: Using immunoblot (IB), we identified an shRNA that was effective against RalGDS and made a stable matched pair of MiaPaCa-2 cells lines. We then transiently transfected the matched pair with validated siRNA against RGL2 (Invitrogen).
Figure 2A:
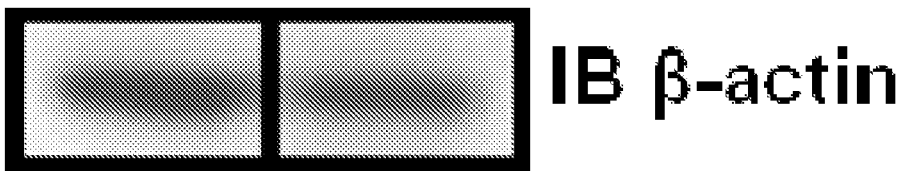

RalGEFS in pancreatic cancer cell transformation: FIG. 2. Inhibition of multiple RalGEFs can sometimes have a synergistic inhibitory effect on growth in agar of pancreatic carcinoma cells. We identified an shRNA that was effective against RalGDS and made a stable matched pair of MiaPaCa-2 cells lines (FIG. 2A). We then transiently transfected the matched pair with validated siRNA against RGL2 (Invitrogen). Soft agar growth inhibition was then measured for the set of 4 cell systems. No effect on normal cell growth in 2D culture was observed (data not shown).

Figure 2B:
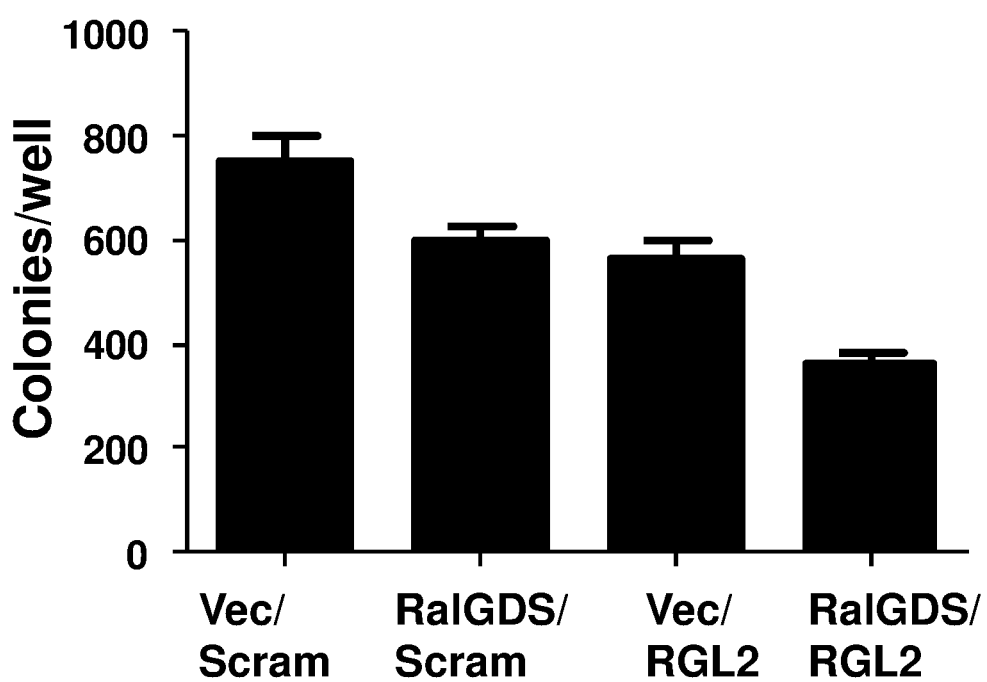
FIG. 2B: Soft agar growth inhibition was then measured for the set of 4 cell systems (scrambled/scrambled; shRalGDS/scrambled; scrambled/SiRGL2; and shRalGDS/SiRGL2). No effect on normal cell growth in 2D culture was observed (data not shown).

MiaPaCa-2 cells express only the RalGDS and RGL2 GEF family members. Stable shRNA inhibition of RGL2 inhibits the ability of the cells to grow in soft agar and form tumors in mice. We have now generated Mia-PaCa2 cells stably transfected with shRNA against RalGDS that are partially knocked down (FIG. 2A). We then transiently transfected the matched pair +/− shRNA-RalGDS with a pre-validated siRNA against RGL2 to simulate the effects of a pan-RalGEF inhibitor. FIG. 2B shows that single RalGEF knockdown inhibited colony formation but that suppressing both RalGEFs had a greater than additive effect. Thus, blocking the action of multiple RalGEFs can sometimes be more effective than blocking a single RalGEF. Therefore, a small molecule that can act as a pan-RalGEF inhibitor could be effective.

Inhibition of Ras/RalGEF binding—FIG. 3. Some compounds of Formula (I) can be pan-RalGEF inhibitors, as shown by blocking the interaction of K-Ras with RalGDS and with RGL2. HEK-293 cells were co-transfected with HA-activated K-Ras and GFP-RalGDS (FIG. 3A) or RGL2 (FIG. 3B) in the presence of some compounds. The cells were lysed. The compound to be tested was added to the lysate to a final concentration 10 μM, which was then incubated with anti-GFP-beads overnight. The immunoprecipitate (IP) was then analyzed for the presence of Ras by immunoblot (IB). FIG. 3A is an example of raw data. FIG. 3B shows quantification of the RGL2 data with Compounds I-1 and I-2.

Figure 3A:
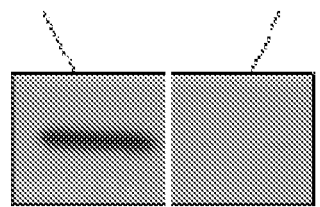
FIG. 3A: An example of raw IP and IB data for HEK-293 cells co-transfected with HA-activated K-Ras and GFP-RalGDS.
Figure 3A:
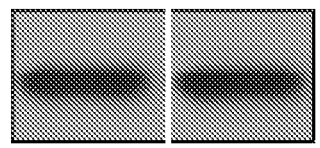
Figure 3A:
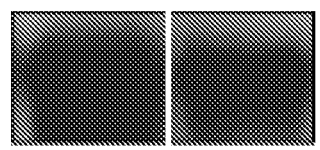
Figure 3B:
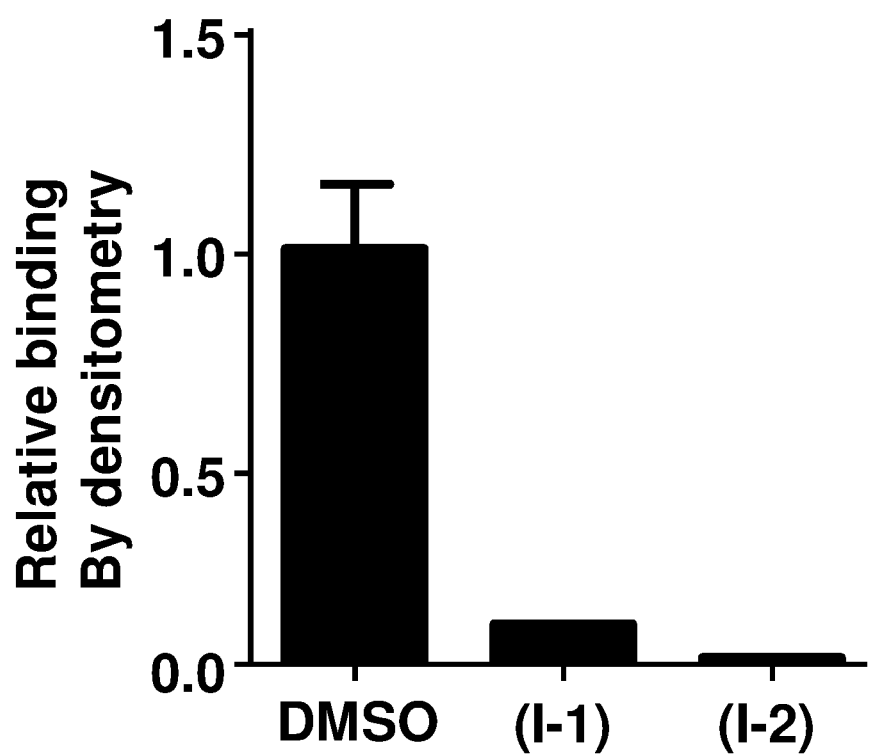
FIG. 3B: This figure shows quantification of the RGL2 data with Compounds I-1 and I-2.

Compound I-1 interferes with the interaction of Ras and RalGEFs. HEK-293 cells were co-transfected with human influenza hemagglutinin (HA) tagged K-Ras 12v and GFP-tagged RalGDS or GFP-tagged RGL2 in the presence or absence of compound I-1. The cells were lysed and the degree of Ras/RalGEF interaction in each sample determined by immunoprecipitation (IP) followed by immunoblot (IB). Compound I-1 (but not carrier) inhibited the stable association of Ras and RalGDS (FIG. 3A). To determine if compound I-1 also inhibited a second RalGEF (RGL2), we performed similar experiments with RGL2. FIG. 3B shows compound I-1 also inhibited RGL2. Thus, compound I-1 appears to be acting as a pan-RalGEF inhibitor. Compound I-2 was also tested using this assay; it was also found to inhibit RGL2 (FIG. 3B).

Figure 4:
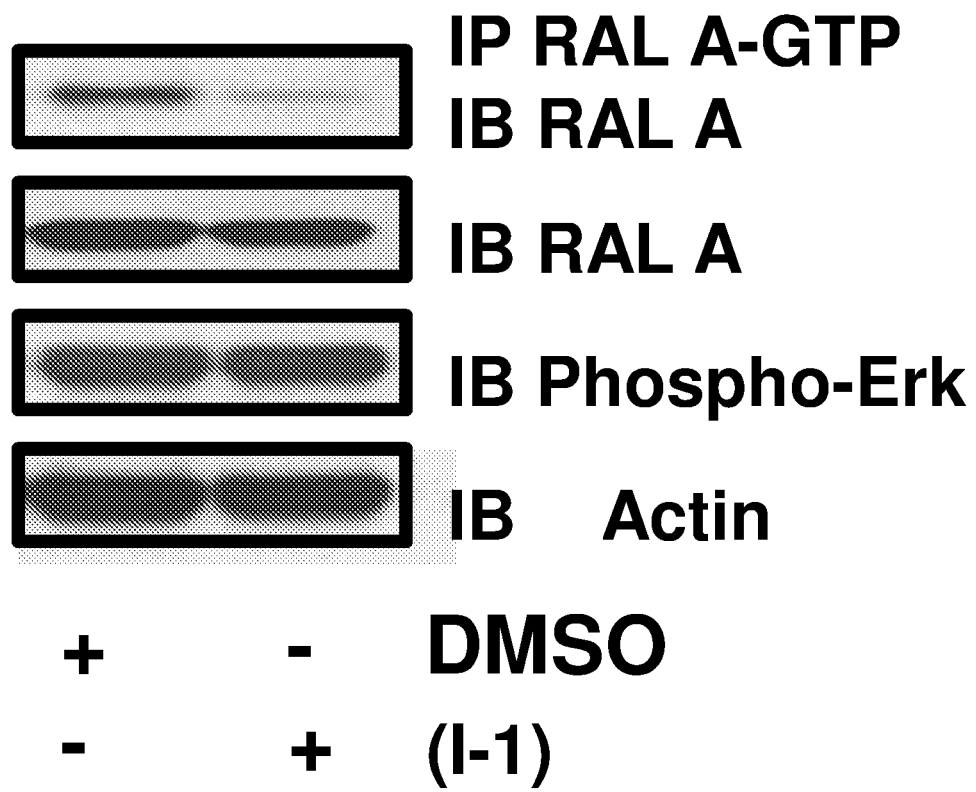
FIG. 4: Specific suppression of Ral activation by some compounds of Formula (I). Cells with endogenous hyperactivated Ras were assayed for endogenous Ral activation in the presence or absence of compounds of Formula (I) (10 μM) using a Cell Biolabs (SanDiego Calif.) kit. The compound to be tested was dissolved in DMSO. DMSO serves as the carrier negative control. IP is immunoprecipitation. IB is immunoblot. Cell lysates were then assayed for the levels of MAPK pathway activation using a phosphoERK antibody; the activity for the DMSO control was the same as the compound treated cells (data not shown). Actin was used as a loading control.

Specific Inhibition of endogenous Ras/RalGEF signaling. FIG. 4. Specific suppression of Ral activation by some compounds of Formula (I). Cells with endogenous hyper-activated Ras were assayed for endogenous Ral activation in the presence or absence of inhibitor (10 μM) using a Cell Biolabs (SanDiego Calif.) kit. Compound I-1 was dissolved in DMSO; DMSO serves as the carrier negative control. IP is immunoprecipitation. IB is immunoblot. Cell lysates were then assayed for the levels of MAPK pathway activation using a phosphoERK antibody. They were the same. Actin is a loading control.

RalGEFs drive Ral into the active, GTP bound form so it can bind its effector RalBP1. Inactive, GDP bound Ral does not bind RalBP1. Commercially available kits available from several vendors use RalBP1 attached to beads as an affinity reagent specific to the active form of Ral. By measuring the level of activated Ral and comparing it to the total levels of Ral, it is possible to measure the state of endogenous Ral activation. We assayed untransfected cells containing endogenous hyper-activated Ras for the effects of compound I-1 treatment on endogenous levels of active Ral levels. Compound I-1 suppressed the levels of endogenous active Ral (GTP bound) (FIG. 4). This effect was specific as no inhibition of the Ras/Raf/MAPK pathway activation was detected (e.g., levels of phospho ERK did not change).

Lack of in vivo toxicity for some compounds of Formula (I): Transgenic knockout studies and shRNA experiments on pancreatic cancer cells show that suppression of the Ras/RalGEF/Ral pathway inhibits the tumorigenic phenotype but does not have a severe impediment on normal cellular function. In tissue culture, compound I-1 had no effect on normal cell growth (FIG. 1) and neither did compound I-2 (data not shown). Preliminary in vivo studies show that doses of 25 mg/kg of compound I-1 have no obvious deleterious effect on mice (e.g., no behavior change and no weight loss) after ip injection over 2 weeks (data not shown).

Figure 5:
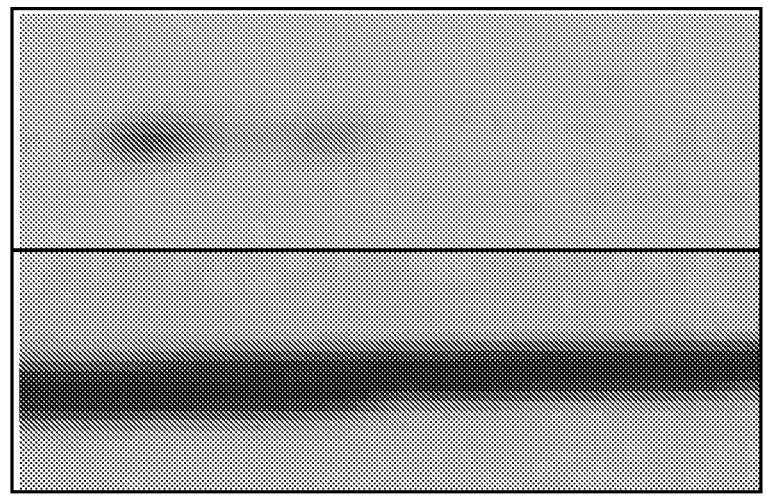
FIG. 5: Some compounds of Formula (I) suppress Ral GTP levels in vivo. NRG mice were provided with s.c. xenografts of Mia-PaCa2 cells. Tissue from the lungs of a carrier treated xenograft mouse and a compound I-1 treated xenograft mouse were assayed for the levels of activated RalA using a pull down assay kit. Compound I-1 appears to suppress the levels of active RalA.

Some compounds of Formula (I) suppress Ral GTP levels in vivo—FIG. 5 NRG mice were provided with s.c. xenografts of Mia-PaCa2 cells. Tissue from the lungs of a carrier treated xenograft mouse and a compound I-1 treated mouse were assayed for the levels of activated RalA using a pull down assay kit using the manufacter's protocol (Cat. #BK040 from Cytoskeleton, Inc., Denver Colo.). The lung tissue from the treated xenograft animal shows reduced levels of active RalA. In particular, FIG. 5 shows that compound I-1 appears to suppress the levels of active Ral bound to GTP in the lung tissue in vivo.

Figure 6A:
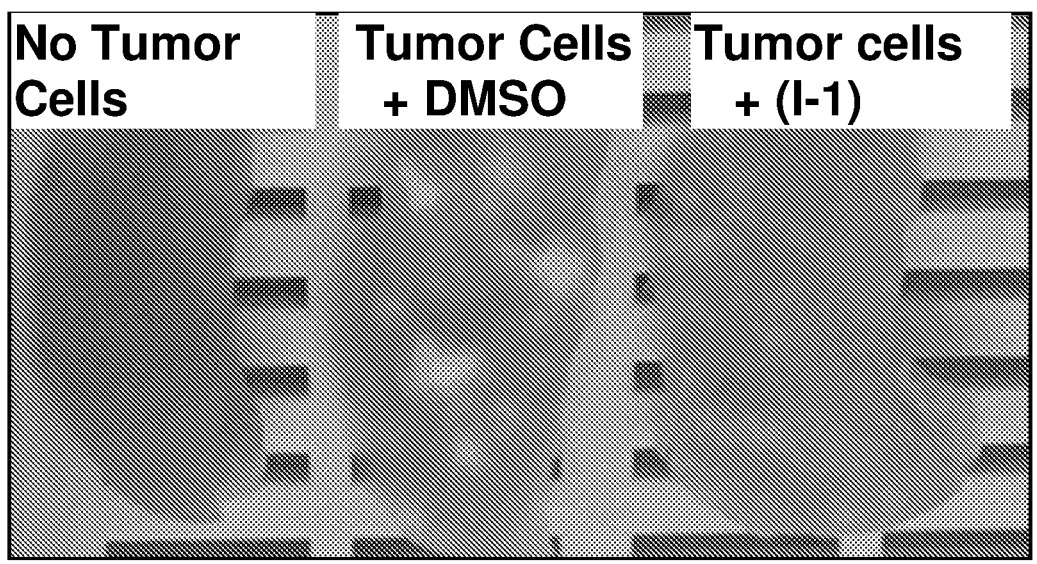
FIG. 6A shows that metastasis was inhibited.
Figure 6B:
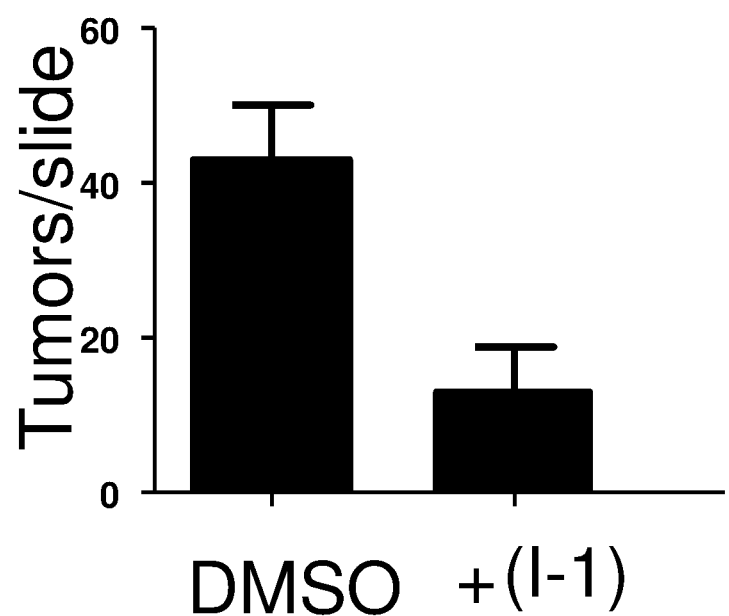
FIG. 6B shows quantification of untreated and treated mice (i.e., the middle lung and the right lung, respectively) of FIG. 6A.

Some compounds of Formula (I) suppress pancreatic cancer cell metastasis—FIG. 6. NRG mice were sub-cutaneously inoculated with PBS ("no tumor cells") or $5 \times 10^6$ Ras driven Mia-PaCa-2 cells. Mice were allowed to recover for 1 week and then injected (ip) with PBS/DMSO carrier or 10 mg/kg of compound I-1 every other day for 2 weeks. One week later, mice were scored for primary tumor growth and lung metastasis. Effects on the primary tumor arising from the sub-cutaneous xenograft (which can be poorly vascularized and sometimes do not take up drugs well) were not obvious. However, metastasis was inhibited, as shown in FIG. 6A. Quantification is shown in FIG. 6B.

The headings used in the disclosure are not meant to suggest that all disclosure relating to the heading is found within the section that starts with that heading. Disclosure for any subject may be found throughout the specification.

It is noted that terms like "preferably," "commonly," and "typically" are not used herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the disclosure, "a" or "an" means one or more than one, unless otherwise specified. As used in the claims, when used in conjunction with the word "comprising" the words "a" or "an" means one or more than one, unless otherwise specified. As used in the disclosure or claims, "another" means at least a second or more, unless otherwise specified. As used in the disclosure, the phrases "such as", "for example", and "e.g." mean "for example, but not limited to" in that the list following the term ("such as", "for example", or "e.g.") provides some examples but the list is not necessarily a fully inclusive list. The word "comprising" means that the items following the word "comprising" may include additional unrecited elements or steps; that is, "comprising" does not exclude additional unrecited steps or elements.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as an illustrative basis for the claims and as a representative basis for teaching one skilled in the art to employ the present invention in any appropriate manner. Indeed, various modifications of the invention in addition to those described herein will become apparent to those skilled in the art from the foregoing description and the accompanying figures. Such modifications are intended to fall within the scope of the appended claims.

What is claimed is:

1. A compound selected from Formula (I)

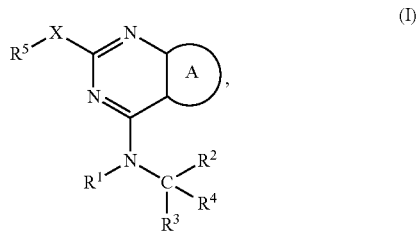

salts of Formula (I), optical isomers of Formula (I), geometric isomers of Formula (I), salts of optical isomers of Formula (I), salts of geometric isomers of Formula (I), and ethers, esters, or amides thereof,
wherein
$R^1$ is H, $C_1$-$C_3$ alkyl, $C_2$-$C_3$ alkenyl, or $C_2$-$C_3$ alkynyl, which $C_1$-$C_3$ alkyl, $C_2$-$C_3$ alkenyl, or $C_2$-$C_3$ alkynyl is optionally substituted with one or more of halogen, hydroxy (—OH), methanoyl (—COH), carboxy (—CO$_2$H), ethynyl (—CCH), cyano (—CN), sulfo (—SO$_3$H), methyl, or ethyl;

$R^2$ is H, halogen, hydroxy (—OH), cyano (—CN), sulfo (—SO$_3$H), $C_1$-$C_3$ alkyl, $C_2$-$C_3$ alkenyl, $C_2$-$C_3$ alkynyl, or $C_1$-$C_2$ alkoxy, which $C_1$-$C_3$ alkyl, $C_2$-$C_3$ alkenyl, $C_2$-$C_3$ alkynyl, or $C_1$-$C_2$ alkoxy is optionally substituted with one or more of halogen, hydroxy (—OH), methanoyl (—COH), carboxy (—CO$_2$H), ethynyl (—CCH), cyano (—CN), sulfo (—SO$_3$H), methyl, or ethyl;

$R^3$ is H, halogen, hydroxy (—OH), cyano (—CN), sulfo (—SO$_3$H), $C_1$-$C_3$ alkyl, $C_2$-$C_3$ alkenyl, $C_2$-$C_3$ alkynyl, or $C_1$-$C_2$ alkoxy, which $C_1$-$C_3$ alkyl, $C_2$-$C_3$ alkenyl, $C_2$-$C_3$ alkynyl, or $C_1$-$C_2$ alkoxy is optionally substituted with one or more of halogen, hydroxy (—OH), methanoyl (—COH), carboxy (—CO$_2$H), ethynyl (—CCH), cyano (—CN), sulfo (—SO$_3$H), methyl, or ethyl;

$R^4$ is H, halogen, —CN, hydroxy (—OH), methanoyl (—COH), carboxy (—CO$_2$H), $C_1$-$C_7$ alkyl, $C_2$-$C_7$ alkenyl, $C_2$-$C_7$ alkynyl, $C_1$-$C_6$ alkoxy, cycloalkyl, heterocyclyl, aryl, or heteroaryl, which methanoyl (—COH), carboxy (—CO$_2$H), $C_1$-$C_7$ alkyl, $C_2$-$C_7$ alkenyl, $C_2$-$C_7$ alkynyl, $C_1$-$C_6$ alkoxy, cycloalkyl, heterocyclyl, aryl, or heteroaryl is optionally substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, or $C_1$-$C_3$ alkoxy;

$R^5$ is —CN, $C_7$ alkyl, $C_2$-$C_7$ alkenyl, $C_2$-$C_7$ alkynyl, $C_1$-$C_6$ alkoxy, cycloalkyl, heterocyclyl, aryl, or heteroaryl, which $C_7$ alkyl, $C_2$-$C_7$ alkenyl, $C_2$-$C_7$ alkynyl, $C_1$-$C_6$ alkoxy, cycloalkyl, heterocyclyl, aryl, or heteroaryl is optionally substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, —CONH$_2$, —CON(CH$_3$)$_2$, $C_1$-$C_3$ alkyl, $C_1$-$C_3$ perfluoronated alkyl, or $C_1$-$C_3$ alkoxy;

X is a bivalent $C_1$-$C_7$ alkyl where 1, 2, or 3 of the $C_1$-$C_7$ alkyl carbons is optionally replaced with a hetero atom which can be the same or different if more than one carbon atom is replaced, and which $C_1$-$C_7$ alkyl or any of the hetero atom replacements, as chemically appropriate, is optionally substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, —CONH$_2$, —CON(CH$_3$)$_2$, $C_1$-$C_3$ alkyl, $C_1$-$C_3$ perfluoronated alkyl, or $C_1$-$C_3$ alkoxy;

ring A is

which can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, —CONH$_2$, —CON(CH$_3$)$_2$, $C_1$-$C_6$ alkyl, $C_1$-$C_6$ perfluoronated alkyl, trifluoromethyl, perfluoroethyl, or $C_1$-$C_5$ alkoxy; and X is not

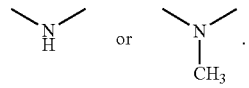

2. The compound of claim 1, wherein $R^1$ is H or $C_1$-$C_3$ alkyl, which $C_1$-$C_3$ alkyl is optionally substituted with one or more of halogen, hydroxy (—OH), methanoyl (—COH), carboxy (—CO$_2$H), cyano (—CN), ethynyl (—CCH), sulfo (—SO$_3$H), methyl, or ethyl.

3. The compound of claim 1, wherein $R^1$ is H, methyl, ethyl, perfluorinated methyl, or perfluorinated ethyl.

4. The compound of claim 1, wherein $R^2$ is H, halogen, hydroxy (—OH), $C_1$-$C_3$ alkyl, or $C_1$-$C_2$ alkoxy, which $C_1$-$C_3$ alkyl or $C_1$-$C_2$ alkoxy is optionally substituted with one or more of halogen, hydroxy (—OH), methanoyl (—COH), carboxy (—CO$_2$H), cyano (—CN), ethynyl (—CCH), sulfo (—SO$_3$H), methyl, or ethyl.

5. The compound of claim 1, wherein $R^2$ is H, halogen, hydroxy (—OH), cyano (—CN), sulfo (—SO$_3$H), methyl, ethyl, methoxy, perfluorinated methyl, or perfluorinated ethyl.

6. The compound of claim 1, wherein $R^3$ is H, halogen, hydroxy (—OH), $C_1$-$C_3$ alkyl, or $C_1$-$C_2$ alkoxy, which $C_1$-$C_3$ alkyl or $C_1$-$C_2$ alkoxy is optionally substituted with one or more of halogen, hydroxy (—OH), methanoyl (—COH), carboxy (—CO₂H), cyano (—CN), ethynyl (—CCH), sulfo (—SO₃H), methyl, or ethyl.

7. The compound of claim 1, wherein $R^3$ is H, halogen, hydroxy (—OH), cyano (—CN), sulfo (—SO₃H), methyl, ethyl, methoxy, perfluorinated methyl, or perfluorinated ethyl.

8. The compound of claim 1, wherein $R^4$ is H, halogen, —CN, hydroxy (—OH), methanoyl (—COH), carboxy (—CO₂H), $C_1$-$C_7$ alkyl, $C_1$-$C_6$ alkoxy, cycloalkyl, heterocyclyl, aryl, or heteroaryl, which methanoyl (—COH), carboxy (—CO₂H), $C_1$-$C_7$ alkyl, $C_1$-$C_6$ alkoxy, cycloalkyl, heterocyclyl, aryl, or heteroaryl is optionally substituted with one or more of halogen, oxo (=O), hydroxy (—OH), methanoyl (—COH), carboxy (—CO₂H), nitro (—NO₂), —NH₂, —N(CH₃)₂, cyano (—CN), ethynyl (—CCH), propynyl, sulfo (—SO₃H), morpholinyl, —CO-morpholin-4-yl, phenyl, —CONH₂, —CON(CH₃)₂, $C_1$-$C_3$ alkyl, $C_1$-$C_3$ perfluoronated alkyl, or $C_1$-$C_3$ alkoxy.

9. The compound of claim 1, wherein $R^4$ is Cl, hydroxy (—OH), methyl, ethyl, $C_{1-5}$ alkyl, $C_3$ alkyl, —CN, ethynyl, —CONH₂, —CON(CH₃)₂, 2-(morpholinyl)ethoxy, —CO-morpholin-4-yl, ethoxy, methoxy, 5-hydroxy pyridyl, 5-hydroxy pyrid-3-yl, indolyl, 1-indolyl, 1,2,3,4-tetrahydroisoquinolyl, 2-1,2,3,4-tetrahydroisoquinolyl, 1,2-methylenedioxyphenyl, 2,3-methylenedioxyphenyl, furyl, 2-furyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, benzyl, pyridyl, 3-pyridyl, methylenedioxyphenyl, perfluorinated methyl, or perfluorinated ethyl.

10. The compound of claim 1, wherein $R^4$ is methyl, ethyl, $C_3$ alkyl, n-propyl, isopropyl, ethoxy, methoxy, 5-hydroxy pyridyl, 5-hydroxy pyrid-3-yl, indolyl, 1-indolyl, 1,2,3,4-tetrahydroisoquinolyl, 2-1,2,3,4-tetrahydroisoquinolyl, furyl, 2-furyl), 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, benzyl, pyridyl, 3-pyridyl, methylenedioxyphenyl, perfluorinated methyl, or perfluorinated ethyl.

11. The compound of claim 1, wherein $R^5$ is —CN, $C_7$ alkyl, $C_1$-$C_6$ alkoxy, cycloalkyl, heterocyclyl, aryl, or heteroaryl, which $C_7$ alkyl, $C_1$-$C_6$ alkoxy, cycloalkyl, heterocyclyl, aryl, or heteroaryl is optionally substituted with one or more of halogen, oxo (=O), hydroxy (—OH), methanoyl (—COH), carboxy (—CO₂H), nitro (—NO₂), —NH₂, —N(CH₃)₂, cyano (—CN), ethynyl (—CCH), propynyl, sulfo (—SO₃H), morpholinyl, —CO-morpholin-4-yl, —CONH₂, —CON(CH₃)₂, $C_1$-$C_3$ alkyl, $C_1$-$C_3$ perfluoronated alkyl, or $C_1$-$C_3$ alkoxy.

12. The compound of claim 1, wherein $R^5$ is phenyl, 5-hydroxy pyridyl, 5-hydroxy pyrid-3-yl, 6-hydroxy pyridyl, 6-hydroxy pyrid-3-yl, 4-hydroxy pyridyl, 4-hydroxy pyrid-3-yl, indolyl, 1-indolyl, 1,2,3,4-tetrahydroisoquinolyl, 2-1,2,3,4-tetrahydroisoquinolyl, 1,2-methylenedioxyphenyl, 2,3-methylenedioxyphenyl, —CO-morpholin-4-yl, —CON(CH₃)₂, —CN, ethynyl, —CONH₂, —CON(CH₃)₂, 2-(morpholinyl)ethoxy, ethoxy, methoxy, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, or 3,5-bis-trifluoromethyl phenyl.

13. The compound of claim 1, wherein $R^5$ is phenyl, 5-hydroxy pyridyl, 5-hydroxy pyrid-3-yl, indolyl, 1-indolyl, 1,2,3,4-tetrahydroisoquinolyl, 2-1,2,3,4-tetrahydroisoquinolyl, 1,2-methylenedioxyphenyl, 2,3-methylenedioxyphenyl, ethoxy, methoxy, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, benzyl, pyridyl, 3-pyridyl, or methylenedioxyphenyl.

14. The compound of claim 1, wherein $R^5$ is phenyl, 5-hydroxy pyridyl, 5-hydroxy pyrid-3-yl, indolyl, 1-indolyl, 1,2,3,4-tetrahydroisoquinolyl, 2-1,2,3,4-tetrahydroisoquinolyl, 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, or 3,5-bis-trifluoromethyl phenyl.

15. The compound of claim 1, wherein X is

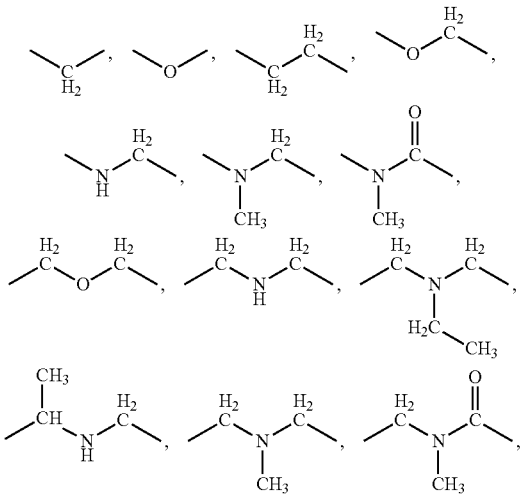

-continued

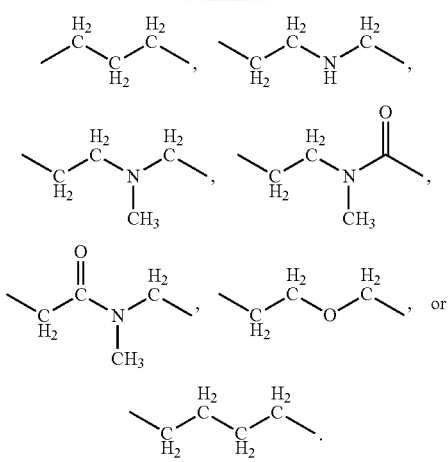

16. The compound of claim 1, wherein ring A is

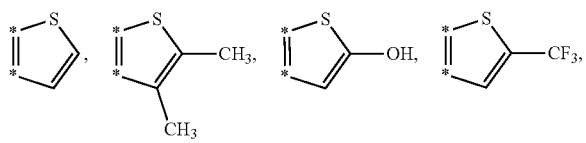

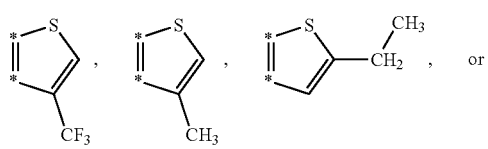

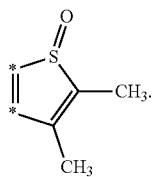

17. The compound of claim 1, wherein R¹ is not H, R² is not H, R³ is not H, R⁴ is not 3-methoxyphenyl, R⁵ is not 3-methoxyphenyl, X is not

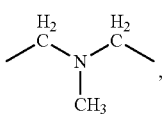

or ring A is not

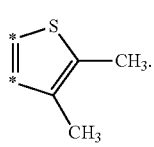

18. The compound of claim 1, wherein compound I-1,

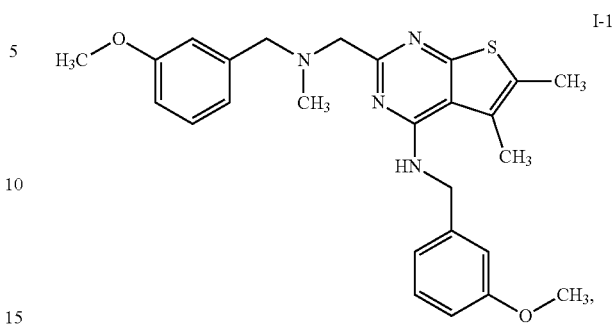

is excluded from Formula (I).

19. A pharmaceutical composition comprising a compound of claim 1 and a pharmaceutically acceptable carrier.

20. A method for providing an animal with a compound comprising one or more administrations of one or more compositions comprising the compound of claim 1, wherein the compositions may be the same or different if there is more than one administration.

21. A method for treating an animal for a disease, comprising one or more administrations of one or more compositions comprising the compound of claim 1, wherein the compositions may be the same or different if there is more than one administration, the animal is in need of the treatment and, the method is for treating pancreatic cancer, pancreatic ductal adenocarcinoma, lung cancer, liver cancer, colorectal cancer, colon cancer, rectal cancer, melanoma, cutaneous malignant melanoma, melanoma tumorigenesis, bladder cancer, prostate cancer, malignant nerve sheath tumors, multiple myeloma, breast cancer, squamous cell carcinoma, head and neck squamous cell carcinoma, lymphoma, leukemia, bone marrow cancer, non-Hodgkin lymphoma, diffuse large B-cell lymphoma, glioblastoma multiforme, endometrial cancer, kidney cancer, basal cell carcinoma, thyroid cancer, neuroblastoma, ovarian cancer, renal cell carcinoma, hepatocellular carcinoma, chronic lymphocytic leukemia (CLL), acute lymphoblastic leukemia, rhabdomyosarcoma, meningioma, gastric cancer, Glioma, oral cancer, nasopharyngeal carcinoma, stomach cancer, uterine cancer, medulloblastoma, cancers that can result in metastasis, cancers resulting from metastasis, or cancerous tumors thereof.

22. A method for preparing a compound of claim 1 comprising, (a) reacting a compound of Formula (II) with a compound of Formula (III) to result in a mixture comprising a compound of Formula (IV);

(b) reacting a compound of Formula (IV) with a suitable compound to convert an oxo to a halogen to result in a mixture comprising a compound of Formula (V);

(c) reacting a compound of Formula (V) with a compound of Formula (VI); and;

(d) recovering Formula (I), wherein Formula (II) is

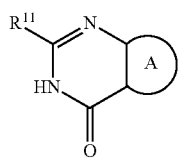
(II)

where $R^{11}$ is a halogen or —CH$_2$-halogen;
Formula (III) is $R^5$—X—H (III);
Formula (IV) is

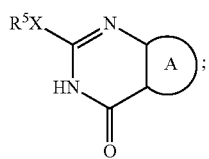
(IV)

Formula (V) is

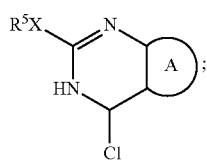
(V)

and
Formula (VI) is

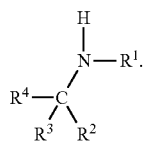
(VI)

23. The compound of claim 1, wherein ring A is substituted with one or more of halogen, oxo (=O), hydroxy (—OH), methanoyl (—COH), carboxy (—CO$_2$H), nitro (—NO$_2$), —NH$_2$, —N(CH$_3$)$_2$, ethynyl (—CCH), propynyl, sulfo (—SO$_3$H), morpholinyl, —CO-morpholin-4-yl, —CONH$_2$, —CON(CH$_3$)$_2$, C$_1$-C$_6$ alkyl, C$_1$-C$_6$ perfluorinated alkyl, trifluoromethyl, perfluoroethyl, or C$_1$-C$_5$ alkoxy.

24. The pharmaceutical composition of claim 19, wherein the amount of the compound is from about 0.0001% (by weight total composition) to about 50%.

25. The pharmaceutical composition of claim 19, wherein the pharmaceutical composition comprises a formulary ingredient, an adjuvant, or a carrier.

26. The method of claim 20, wherein at least one of the one or more compositions further comprises a formulary ingredient.

27. The method claim 20, wherein at least one of the one or more administrations comprises parenteral administration, a mucosal administration, intravenous administration, subcutaneous administration, topical administration, intradermal administration, oral administration, sublingual administration, intranasal administration, or intramuscular administration.

28. The method claim 20, wherein if there is more than one administration at least one composition used for at least one administration is different from the composition of at least one other administration.

29. The method of claim 20, wherein the compound of at least one of the one or more compositions is administered to the animal in an amount of from about 0.01 mg/kg animal body weight to about 15 mg/kg animal body weight.

30. The method of claim 20, wherein the animal is a human, a rodent, or a primate.

31. The method of claim 21, wherein at least one of the one or more compositions further comprises a formulary ingredient.

32. The method of claim 21, wherein at least one of the one or more administrations comprises parenteral administration, a mucosal administration, intravenous administration, subcutaneous administration, topical administration, intradermal administration, oral administration, sublingual administration, intranasal administration, or intramuscular administration.

33. The method of claim 21, wherein if there is more than one administration at least one composition used for at least one administration is different from the composition of at least one other administration.

34. The method of claim 21, wherein the compound of at least one of the one or more compositions is administered to the animal in an amount of from about 0.005 mg/kg animal body weight to about 50 mg/kg animal body weight.

35. The method of claim 21, wherein the animal is a human, a rodent, or a primate.

36. The method of claim 21, wherein the animal is in need of the treatment.

37. The method of claim 21, wherein the method is for treating pancreatic cancer, pancreatic ductal adenocarcinoma, lung cancer, liver cancer, colorectal cancer, colon cancer, rectal cancer, melanoma, cutaneous malignant melanoma, melanoma tumorigenesis, bladder cancer, malignant nerve sheath tumors, multiple myeloma, breast cancer, squamous cell carcinoma, head and neck squamous cell carcinoma, ovarian cancer, prostate cancer, medulloblastoma, cancers that can result in metastasis, cancers resulting from metastasis, or cancerous tumors thereof.

38. The method of claim 21, wherein the method is for treating pancreatic cancer, pancreatic ductal adenocarcinoma, lung cancer, liver cancer, ovarian cancer, prostate cancer, medulloblastoma, cancers that can result in metastasis, cancer resulting from metastasis of pancreatic cancer, lung cancer resulting from metastasis, or cancerous tumors thereof.

39. The method of claim 22, wherein $R^{11}$ is —CH$_2$-halogen.

40. The method of claim 22, wherein the suitable compound to convert an oxo to a halogen is POCl$_3$ or POBr$_3$.

* * * * *